: US009017716B2

United States Patent
Satake

(10) Patent No.: US 9,017,716 B2
(45) Date of Patent: *Apr. 28, 2015

(54) OPHTHALMIC LENS

(75) Inventor: Kohsuke Satake, Kasugai (JP)

(73) Assignee: Menicon Co., Ltd., Aichi (JP)

( * ) Notice: Subject to any disclaimer, the term of this patent is extended or adjusted under 35 U.S.C. 154(b) by 526 days.

This patent is subject to a terminal disclaimer.

(21) Appl. No.: 13/382,642

(22) PCT Filed: Jul. 6, 2010

(86) PCT No.: PCT/JP2010/061448
§ 371 (c)(1),
(2), (4) Date: Mar. 2, 2012

(87) PCT Pub. No.: WO2011/004808
PCT Pub. Date: Jan. 13, 2011

(65) Prior Publication Data
US 2012/0148519 A1 Jun. 14, 2012

(30) Foreign Application Priority Data

Jul. 8, 2009 (JP) ................................ 2009-161888

(51) Int. Cl.
*A61K 31/787* (2006.01)
*A61P 31/04* (2006.01)
*C08F 220/34* (2006.01)
*A61L 27/16* (2006.01)
*A61L 27/18* (2006.01)
*A61L 27/52* (2006.01)
*C08F 226/06* (2006.01)
*G02B 1/04* (2006.01)

(52) U.S. Cl.
CPC ............... *C08F 220/34* (2013.01); *A61L 27/16* (2013.01); *A61L 27/18* (2013.01); *A61L 27/52* (2013.01); *C08F 226/06* (2013.01); *G02B 1/043* (2013.01)

(58) Field of Classification Search
CPC ....... C08F 220/004; G02B 1/043; A61L 12/14
USPC ............................. 424/78.04, 78.31; 528/26
See application file for complete search history.

(56) References Cited

U.S. PATENT DOCUMENTS 5,270,415 A    12/1993   Sulc et al.

FOREIGN PATENT DOCUMENTS

| JP | 04-076518 | 3/1992 |
|----|-----------|--------|
| JP | 06-102472 | 4/1994 |
| JP | 06-508858 | 10/1994 |
| JP | 06-337378 | 12/1994 |
| JP | 2004-070066 | 3/2004 |
| JP | 2004-346291 | 12/2004 |
| JP | 2006-162673 | 6/2006 |
| JP | 2007-219067 | 8/2007 |
| JP | 2008-122937 | 5/2008 |
| WO | WO 2008/038719 | 4/2008 |
| WO | WO 2008/038721 | 4/2008 |

OTHER PUBLICATIONS

Amajjahe et al., "Switching the Solubility of PMMA Bearing Attached Cyclodextrin-Moieties by Supramolecular Interactions with Ionic Liquids", Macromol. Rapid Commun, vol. 30, No. 11, Jun. 2, 2009, pp. 904-908, XP002687179.
Amajjahe et al., "Supramolecular Controlled Pseudo-LCST Effects of Cyclodextrin-Complexed Poly(ionic liquids)", Macromolecules, vol. 41, No. 9, Apr. 8, 2008, pp. 3250-3253, XP002687180.
Li et al., "Swelling behavior of amphiphilic gets based on hydrophobically modified dimethylaminoethyl methacrylate", Polymer, vol. 50, No. 20, Sep. 23, 2009, pp. 4888-4894, XP002687181.
Extended European Search Report for corresponding EP Application No. 10797119.4-2109, Nov. 28, 2012.
International Search Report for corresponding International Application No. PCT/JP2010/061448, Aug. 3, 2010.

*Primary Examiner* — Walter Webb
(74) *Attorney, Agent, or Firm* — Oliff PLC

(57) ABSTRACT

The present invention is directed to an ophthalmic lens integrally formed with a hydrogel, the hydrogel including a copolymer obtained from a composition containing (A) an ionic compound including a cation having a polymerizable functional group, and a fluorine-containing anion (hereinafter, referred to as (A) ionic compound), and (B) a hydrophilic compound having a polymerizable functional group.

9 Claims, No Drawings

OPHTHALMIC LENS

TECHNICAL FIELD

The present invention relates to an ophthalmic lens.

BACKGROUND ART

Hydrogels produced by swelling a polymer compound such as polyhydroxyethyl methacrylate in a water-based solvent have elasticity similar to matter in living bodies, and impart superior wearing feel; therefore, they are used for ophthalmic lenses such as contact lenses. Examples of typical hydrogels used in an ophthalmic lens include silicone hydrogels prepared by copolymerizing a silicone monomer (or macromer) with a hydrophilic monomer.

However, waste products in the lacrimal fluid and bacteria in the air are likely to attach to the ophthalmic lens in which such a hydrogel is used, and thus proliferation of bacteria in hydrogel systems are likely to occur, whereby eye diseases and the like may be developed. To cope with such disadvantages, cleanliness of the lens can be maintained by periodically executing disinfection such as boiling. However, such a treatment is laborious, and the disinfecting effect does not persist for a long period of time. In addition, a method of immersing in a cleaning and preservative solution for contact lenses, referred to as "multipurpose solution", containing an antiseptic component was proposed, and has become broadly prevalent. However, in addition to the disadvantages similar to those described above, wearing of contact lenses results in disadvantages of inferior effect of suppressing bacterial infection during wearing due to bleeding out of the antibacterial component together with the lacrimal fluid. Therefore, development of a technique of imparting an antibacterial effect to the ophthalmic lens per se has been in progress.

Also, an ophthalmic lens in which a hydrogel is used generally has a high moisture content, and the moisture gradually volatilizes during the lens is kept wearing, accompanied by absorption of the lacrimal fluid into the hydrogel. Therefore, feeling of dryness is likely to be provided, and as a result, wearing feel may be deteriorated. The moisture content is almost in a proportional relationship with a coefficient (i.e., linear swelling coefficient) representing the degree of change in size between the state prior to moisturization of the hydrogel (i.e., xerogel) and the state after swelling to reach equilibrium by absorbing the moisture. Therefore, reduction of the linear swelling coefficient in water as low as possible leads to decrease in the moisture content of the hydrogel. Accordingly, an ophthalmic lens having a low linear swelling coefficient, and is capable of achieving comfortable wearing feel for a long period of time has been demanded.

Contact lenses having antibacterial properties are disclosed in, for example, Japanese Unexamined Patent Application, Publication No. H4-76518. The antibacterial contact lenses are produced by kneading an antibacterial ceramic carrying a metal selected from silver, zinc and copper into a base material such as a hydrogel, or by coating a base material with an antibacterial ceramic, thereby imparting an antibacterial property to the contact lens. This antibacterial effect is exerted by generation of active oxygen due to the silver, zinc or copper metal, followed by killing of common bacteria and mold by the generated active oxygen. However, such a contact lens is disadvantageous in that use for a long period of time leads to impairment of the antibacterial property with time, as a result of elution or detachment of the antibacterial ceramic or the metal carried. In addition, Japanese Unexamined Patent Application, Publication No. H4-76518 does not disclose means for reducing the linear swelling coefficient of the contact lens in water.

Furthermore, for example, Japanese Unexamined Patent Application, Publication No. H6-337378 discloses a hydrogel that includes a copolymer obtained from a monomer mixture containing a hydrocarbon-group-containing (meth) acrylate having a hydroxyl group and may have an in-chain ether linkage, and a monomer having a quaternary ammonium salt in the side chain, as well as a soft contact lens formed from this hydrogel. However, although this hydrogel has a certain level of antibacterial properties per se, due to having very high hydrophilicity, when a cationic monomer such as a quaternary ammonium salt having a halide ion as a counter ion is copolymerized with other additional hydrophilic monomer to produce a hydrogel results in a too great linear swelling coefficient, thereby leading to failure in solving the foregoing problems. In addition, when the solubility of the employed monomers with one another is insufficient, and a hydrophobic compound must be further added to a system of copolymerization of a hydrophilic monomer with a monomer having a quaternary ammonium salt, in particular, the transparency is unsatisfactory. Moreover, Japanese Unexamined Patent Application, Publication No. H6-337378 does not disclose means for reducing the linear swelling coefficient when this hydrogel is used for an ophthalmic lens.

On the other hand, for example, Japanese Unexamined Patent Application, Publication No. 2008-122937 discloses an ophthalmic lens having a base layer part made of a silicone hydrogel containing a silicone component, and a superficial layer part made of a polymer compound including monomer units having at least one ammonium group in the molecule. Also, it is described that such an ophthalmic lens has an antibacterial property, and the antibacterial property is not reduced even if washing with water or the like is carried out. However, since this ophthalmic lens has a two-layer structure including a base layer part and a superficial layer part, it is manufactured by producing the base layer part first, and then forming the superficial layer part on the surface thereof. Therefore, multiple steps are included in manufacture, and thus the manufacture equipment becomes complicated, thereby leading to increase in the cost. Also, Japanese Unexamined Patent Application, Publication No. 2008-122937 does not disclose means for reducing the linear swelling coefficient of a contact lens.

Therefore, development of an ophthalmic lens having sufficient antibacterial property that is persistent even if used for a long period of time and also having practical transparency, with a low linear swelling coefficient in water has been strongly desired, which is capable of providing comfortable wearing feel and which can be easily manufactured.

PRIOR ART DOCUMENTS

Patent Documents

Patent Document 1: Japanese Unexamined Patent Application, Publication No. H4-76518
Patent Document 2: Japanese Unexamined Patent Application, Publication No. H6-337378
Patent Document 3: Japanese Unexamined Patent Application, Publication No. 2008-122937

SUMMARY OF THE INVENTION

Problems to be Solved by the Invention

The present invention was made in order to overcome the disadvantage as described in the foregoing. More specifically, a main object of the present invention is to provide an ophthalmic lens having superior antibacterial property and transparency, with a sufficiently low linear swelling coefficient, and being capable of providing comfortable wearing feel. In addition, another object of the present invention is to provide an ophthalmic lens which may be suitably used as a contact lens.

Means for Solving the Problems

The present inventors thoroughly investigated, and consequently found that an ophthalmic lens having high transparency, and low linear swelling coefficient, and superior antibacterial property can be obtained by using a hydrogel formed from an ionic compound including a cation having a polymerizable functional group, and a fluorine-containing anion. Thus, the present invention was accomplished.

An aspect of the invention made in order to solve the foregoing problems provides an ophthalmic lens integrally formed with a hydrogel, the hydrogel including a copolymer obtained from a composition comprising (A) an ionic compound including a cation having a polymerizable functional group, and a fluorine-containing anion (hereinafter, referred to as ionic compound (A)), and (B) a hydrophilic compound having a polymerizable functional group.

The ophthalmic lens exhibits a potent antibacterial property, and can effectively reduce the occurrence of eye diseases and the like owing to the cation and the fluorine-containing anion present as components of the hydrogel. In addition, since the ophthalmic lens is integrally formed in the entirety of the lens from the hydrogel lens, production of a base layer part and a superficial layer part in separate steps is not necessary, whereby manufacturing step and the equipment can be simplified, and thus reduction of the manufacturing cost is enabled. Moreover, due to containing the fluorine-containing anion in the hydrogel, the ophthalmic lens has significantly low linear swelling coefficient in water, whereby comfortable wearing feel can be provided. It is to be noted that the "hydrophilic compound having a polymerizable functional group" that is the component (B) does not contain a silicone compound as a component (C) described later.

In the ophthalmic lens, the cation having a polymerizable functional group in the ionic compound (A) is preferably at least one selected from the set consisting of an imidazolium ion, a pyridinium ion, and a quaternary ammonium ion. By using a combination of such a cation with a fluorine-containing anion, production of a hydrogel having superior antibacterial property, and having a linear swelling coefficient kept at low level is enabled. Moreover, also in the case in which addition of a hydrophobic compound allowing for copolymerization is intended, a transparent hydrogel can be produced due to having sufficient affinity.

In the ophthalmic lens, the ionic compound (A) constituting the copolymer is preferably at least one selected from the set consisting of compounds represented by the following formulae (I), (II) and (III). By using such an ionic compound, production of a hydrogel having high antibacterial property, and having a linear swelling coefficient kept at low level is enabled. Moreover, also in the case in which addition of a hydrophobic compound when allowing for copolymerization is intended, a transparent hydrogel can be produced due to having sufficient affinity.

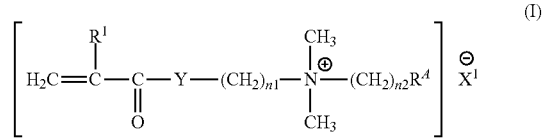

(in the formula (I), $R^1$ represents —H or —$CH_3$; Y represents —O— or —NH—; n1 is of 1 to 18; n2 is of 1 to 25; $X^1$ represents an anion including fluorine; and $R^A$ represents a hydrogen atom, —OH or —COOH.)

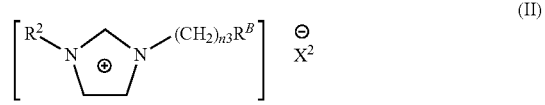

(in the formula (II), $R^2$ represents —CH=$CH_2$, —$CH_2$—CH=$CH_2$ or a group represented by the formula (IV); n3 is of 1 to 25; $X^2$ represents an anion including fluorine; and $R^B$ represents a hydrogen atom, —OH or —COOH.)

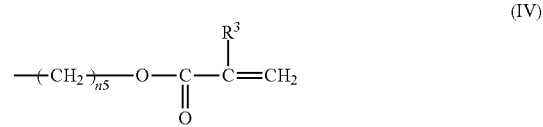

(in the formula (IV), $R^3$ represents —H or —$CH_3$; and n5 is an of 0 to 24.)

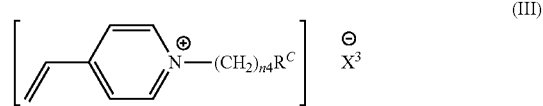

(in the formula (III), n4 is of 1 to 25; $X^3$ represents an anion including fluorine; and $R^C$ represents a hydrogen atom, —OH or —COOH.)

In the ophthalmic lens, the fluorine-atom-containing anion in the ionic compound (A) constituting the copolymer is preferably at least one selected from the set consisting of anions represented by the following formula (V), (VI) and (VII). When the anion having such a structure is used as the fluorine atom-containing anion, a transparent ophthalmic lens having superior antibacterial property and a low linear swelling coefficient in water can be obtained while maintaining high chemical affinity between the ionic compound and the hydrophilic compound having a polymerizable functional group.

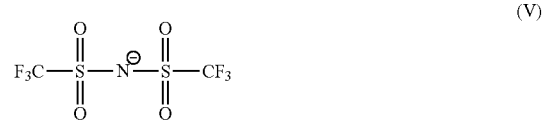

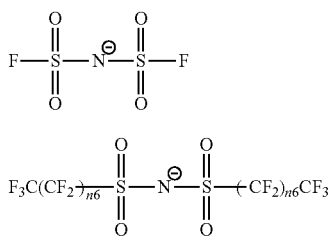

(VII)

$$F_3C(CF_2)_{\overline{n6}}\overset{O}{\underset{O}{\overset{\|}{S}}}-N^{\ominus}-\overset{O}{\underset{O}{\overset{\|}{S}}}-(CF_2)_{n6}CF_3$$

(in the formula (VII), n6 is of 1 to 3.)

In the ophthalmic lens, it is preferred that the composition further contains a silicone compound (C) in addition to the ionic compound (A) and component (B). Use of a silicone compound as a component of the composition enables to prevent development of eye diseases effectively by improving oxygen permeability of the ophthalmic lens to relieve strain on eyes.

In the ophthalmic lens, the ionic compound (A) is preferably an ionic liquid. Since ionic liquids are flame retardant and have a high thermal decomposition temperature, a hydrogel that is superior in thermal stability can be obtained by using an ionic liquid as the ionic compound (A). In addition, since the ionic liquid is in a state of liquid at normal temperatures, it is miscible with other monomer without need of a large quantity of a solvent, and additionally the handling can be more convenient as compared with the state of solid. Still further, due to comparatively high ion density and polarity, ionic compound molecules failed to participate in the copolymerization reaction stably coordinate to the polar group of the copolymer in the ionic liquid, and thus an ophthalmic lens capable of exhibiting superior antibacterial property for a long period of time, and a low linear swelling coefficient in water can be obtained.

The linear swelling coefficient in water of the ophthalmic lens is preferably less than the linear swelling coefficient in water of the ophthalmic lens in which the fluorine-containing anion was replaced for an anion not containing fluorine. Moreover, the difference between the linear swelling coefficient in water of the ophthalmic lens in which the fluorine-containing anion was replaced for an anion not containing fluorine and the linear swelling coefficient in water of the ophthalmic lens before the replacement is preferably no less than 0.005 and no greater than 0.1. By using the fluorine-atom-containing anion as the anion in the ionic compound (A) in the ophthalmic lens, the linear swelling coefficient in water can be reduced as compared with the case in which an anion not containing fluorine was used, whereby more comfortable wearing feel can be achieved, and preventing deterioration of wearing feel and eye diseases such as failures due to dry eyes and the like, which may occur based on ease in drying resulting from the ophthalmic lens having a high linear swelling coefficient is enabled. It is to be noted that the "linear swelling coefficient" as referred to herein means the proportion of the diameter of the ophthalmic lens subsequently immersed in distilled water at 20° C. and reached a state of equilibrium in terms of swelling, with respect to the diameter of the ophthalmic lens after completing the copolymerization reaction of the ionic compound (A) and component (B) and represented by the proportion. More specifically, the linear swelling coefficient is represented by the formula of:

linear swelling coefficient=(diameter of the lens after hydration)/(diameter of the lens before the hydration).

The ophthalmic lens is preferably for use as a contact lens. The ophthalmic lens of the present invention exhibits a potent antibacterial effect for a long period of time, with a low linear swelling coefficient in water, and has transparency; therefore, it can be suitably used as a contact lens.

Effects of the Invention

As explained in the foregoing, the ophthalmic lens of the present invention achieves prolonged superior antibacterial property owing to a combination of the cation and the fluorine-containing anion included as components of a hydrogel. In addition, since the ophthalmic lens is integrally formed in the entirety of the lens, manufacturing step and the equipment can be simplified, and thus reduction of the manufacturing cost is enabled. Moreover, owing to the presence of the cation and the fluorine-containing anion, the ophthalmic lens of the present invention has significantly low linear swelling coefficient in water, thereby capable of providing comfortable wearing feel, and prevention of eye diseases is enabled.

DESCRIPTION OF EMBODIMENTS

Hereinafter, embodiments of the ophthalmic lens according to the present invention are explained in detail.

The ophthalmic lens of the present invention integrally formed with a hydrogel including a copolymer obtained from a composition containing an ionic compound (A) including a cation having a polymerizable functional group, and a fluorine-containing anion, and a hydrophilic compound (B) having a polymerizable functional group. Each component of the ophthalmic lens is explained below in order.

<Ionic Compound (A)>

The "cation having a polymerizable functional group" that constitutes the ionic compound (A) is not particularly limited as long as it has a polymerizable functional group, and can form an ionic bond with the fluorine-containing ion provided as a counter ion. Examples of the cation include a pyrrolidinium ion, a pyridinium ion, an imidazolium ion, a pyrazolium ion, a benzimidazolium ion, an indolium ion, a carbazolium ion, a quinolinium ion, a piperidinium ion, a piperazinium ion, a quaternary ammonium ion, and the like. These cations may be used alone, or a plurality of types of the cations may be used in combination.

Although the polymerizable functional group included in the cation is not particularly limited, typical examples are ethylenic unsaturated groups. Specific examples of the ethylenic unsaturated group include a terminal vinyl group, an allyl group, a (meth)acryl group, an α-substituted acryl group, an ethylene group, and a styryl group.

Among these cations, an imidazolium ion, a pyridinium ion and a quaternary ammonium ion are preferred, and an imidazolium ion and a quaternary ammonium ion are particularly preferred. By using a combination of at least one of the cations with a fluorine-containing anion as the ionic compound, production of a hydrogel having a linear swelling coefficient kept at low level is enabled. Moreover, also in the case in which addition of a hydrophobic compound when allowing for copolymerization of the ionic compound (A) and the component (B) is intended, a transparent hydrogel can be produced due to having sufficient affinity. Among the imidazolium ion and the quaternary ammonium ion, cations that constitute the compound represented by the above formulae (I) and (II) are most preferred.

The fluorine-containing anion that constitutes the ionic compound (A) is not particularly limited as long as it is an ion containing fluorine. Examples of the fluorine-containing anion include $BF_4^-$, $PF_6^-$, $AsF_6^-$, $SbF_6^-$, $(FSO_2)_2N^-$, $(CF_3SO_2)_2N^-$, $(C_2F_5SO_2)_2N^-$, $(C_3F_7SO_2)_2N^-$, $(C_4F_9SO_2)_2N^-$, $(CF_3SO_2)_3C^-$, $(C_2F_5SO_2)_3C^-$, $(C_3F_7SO_2)_3C^-$, $(C_4F_9SO_2)_3C^-$, $F^-$, $(HF)_n^-$, $CF_3SO_3^-$, $CF_3COO^-$, and the like. Among these fluorine-containing anions, $(CF_3SO_2)_2N^-$ (bis(trifluoromethanesulfonyl)imide anion) represented by the above formula (V), or $(FSO_2)_2N^-$ (bis(fluorosulfonyl)imide anion) represented by the formula (VI) is particularly preferred. By using the anion having such a structure in combination with the cation having a polymerizable functional group as the ionic compound, an ophthalmic lens having significantly superior antibacterial property and a low linear swelling coefficient in water can be obtained.

The ionic compound (A) is preferably in the state of an ionic liquid. The ionic liquid is flame retardant and has a high thermal decomposition temperature. Therefore, a hydrogel that is superior in thermal stability can be obtained by using an ionic liquid as the ionic compound (A), and allowing for copolymerization with the component (B). In addition, since the ionic liquid is in the state of liquid at normal temperatures, it is miscible with other monomer without need of a large quantity of a solvent, and additionally the handling can be more convenient as compared with the state of solid. Still further, due to comparatively high ion density and polarity, ionic compound molecules failed to participate in the copolymerization reaction stably coordinate to the polar group of the copolymer in the ionic liquid, and thus obtaining an ophthalmic lens capable of exhibiting superior antibacterial property for a long period of time, and a low linear swelling coefficient in water is enabled.

The proportion of the ionic compound (A) used in the composition is not particularly limited, but is preferably no less than 0.1% by mass and no greater than 30% by mass, and more preferably no less than 0.2% by mass and no greater than 20% by mass. When the proportion of the ionic compound (A) is no less than 0.1% by mass, superior antibacterial property can be obtained. Whereas, when the proportion of the ionic compound (A) is no greater than 30% by mass, deterioration of stability and transparency of the hydrogel can be inhibited.

<(B) Hydrophilic Compound Having a Polymerizable Functional Group>

The hydrophilic compound having a polymerizable functional group as the component (B) is not particularly limited as long as it is capable of copolymerizing with the ionic compound which is the ionic compound (A) containing a cation having a polymerizable functional group as a constitutional component, and has a hydrophilicity group. Examples of the polymerizable functional group include similar ones presented as examples of cation that constitutes the ionic compound (A).

Specific examples of the hydrophilic compound having a polymerizable functional group include carboxylic acids such as (meth)acrylic acid, itaconic acid, crotonic acid, and vinylbenzoic acid;

(meth)acrylates having a hydroxyl group such as hydroxymethyl (meth)acrylate, 2-hydroxyethyl (meth)acrylate, 2-hydroxypropyl (meth)acrylate, 2,3-dihydroxypropyl (meth)acrylate, mono(meth)acrylate of polyethylene glycol, and mono(meth)acrylate of polypropylene glycol;

(meth)acrylamides such as (meth)acrylamide, N-methyl (meth)acrylamide, N-ethyl(meth)acrylamide, N-hydroxyethyl(meth)acrylamide, N,N-dimethyl(meth)acrylamide, N,N-diethyl(meth)acrylamide, and N-ethyl-N-aminoethyl (meth)acrylamide;

(alkyl)aminoalkyl acrylate such as 2-dimethylaminoethyl acrylate, and 2-butylaminoethyl acrylate;

pyrrolidones having a polymerizable functional group such as N-vinyl-3-methyl-2-pyrrolidone, N-vinyl-4-methyl-2-pyrrolidone, N-vinyl-5-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-(meth)acryloylpyrrolidone, N-(meth) acryloyloxyethylpyrrolidone, 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-i-propyl-3-methylene-2-pyrrolidone, 1-i-propyl-5-methylene-2-pyrrolidone, 1-n-butyl-3-methylene-2-pyrrolidone, and 1-t-butyl-3-methylene-2-pyrrolidone;

N-vinylpiperidones such as N-vinyl-2-piperidone, N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, and N-vinyl-4,4-dimethyl-2-piperidone;

N-vinyllactams such as N-vinyl-2-caprolactam, N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, and N-vinyl-3,5,7-trimethyl-2-caprolactam;

N-vinylamides such as N-vinylformamide, N-vinyl-N-methylformamide, N-vinyl-N-ethylformamide, N-vinylacetamide, N-vinyl-N-methylacetamide, and N-vinyl-N-ethylacetamide;

other hydrophilic compounds having a polymerizable functional group such as aminostyrene, hydroxystyrene, vinyl acetate, glycidyl acrylate, allyl glycidyl ether, vinyl propionate, N-vinylimidazole, N-vinylpiperidine, N-vinylsuccinimide, N-vinylphthalimide, N-(meth)acryloylpiperidine, and N-(meth)acryloylmorpholine, and the like.

Among these hydrophilic compounds having a polymerizable functional group, (meth)acrylates having a hydroxyl group and (meth)acrylamides are preferred in light of mechanical characteristics and storage stability of the resulting hydrogel. Also, when the silicone compound described later is used, pyrrolidone derivatives in which the polymerizable group is a methylene group, and nitrogen-substituted (meth)acrylamides are preferred in light of improvement of solubility with the silicone compound in the composition, along with capability of imparting wettability with water, lubricating property and readily wetting property to the surface of the resulting lens. These hydrophilic compounds having a polymerizable functional group may be used alone, or a plurality of types thereof may be used. In a system in which a component such as vinyl acetate that is hydrolyzed by an acid or a base is used, further flexibility and wettability with water can be imparted to the ophthalmic lens by subjecting to a treatment with the acid or base after producing the ophthalmic lens.

The proportion of the component (B) in the composition is not particularly limited, but is preferably no less than 30% by mass and no greater than 95% by mass, and more preferably no less than 40% by mass and no greater than 90% by mass. When the proportion of the component (B) is no less than 30% by mass, a hydrogel having sufficient hydrophilicity and being stable can be obtained. When the proportion of the component (B) is no greater than 95% by mass, deterioration of the antibacterial effect and the like by the ionic compound (A) can be inhibited.

<(C) Silicone Compound>

In order to impart superior oxygen permeability and flexibility to the resulting lens, a silicone compound may be added as the silicone compound (C) to the composition. Such a silicone compound is not particularly limited as long as it has a siloxanyl group. Also, the silicone compound may have a polymerizable functional group, and examples of the polymerizable functional group include those similar to examples in the ionic compound (A) and component (B).

The silicone compound as the silicone compound (C) may be represented by, for example, the following formula (VIII).

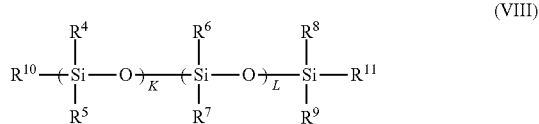
(VIII)

in the formula (VIII), $R^4$, $R^5$, $R^6$, $R^7$, $R^8$, $R^9$, $R^{10}$ and $R^{11}$ each independently represent an alkyl group having 1 to 6 carbon atoms, a fluorine-substituted alkyl group, an alkyl group having at least one amino group, an alkyl group having at least one hydroxyl group, an alkyl group having at least one epoxy group, an alkyl group having at least one carboxyl group, a phenyl group or a hydrogen atom; K is of 10 to 100; L is of 0 to 90; and sum of K and L is of 10 to 100.

Preferable examples of the compound having a polymerizable functional group among the silicone compounds as the silicone compound (C) include compounds having an ethylenic unsaturated group and a polydimethylsiloxane structure via a urethane bond. Due to having a urethane bond and a siloxane moiety, these silicone compounds impart flexibility, elastic resilience and oxygen permeability to the resulting lens, and concomitantly have an effect of enhancing mechanical strength. More specifically, such a silicone compound has an ethylenic unsaturated group that is a polymerizable group at two ends of the molecule, and is copolymerized with other copolymerize component via the polymerizable group. Therefore, imparting not only physical strengthening by way of crosslinking of the molecules, but also a reinforcing effect by way of chemical bonds to the lens obtained is enabled.

Typical examples of the compound having an ethylenic unsaturated group and a polydimethylsiloxane structure via an urethane bond include polysiloxane macromonomers represented by the following formula (1):

$$A^1-U^1-(-S^1-U^2-)_n-S^2-U^3-A^2 \quad (1)$$

in the formula (1), $A^1$ is a group represented by the following formula (2); $U^1$ is a group represented by the following formula (4); $S^1$ and $S^2$ are each a group represented by the following formula (5); $U^2$ is a group represented by the following formula (6); $U^3$ is a group represented by the following formula (7); $A^2$ is a group represented by the following formula (3); and n is of 0 to 10;

$$—Y^{21}—Z^{21}—R^{21}— \quad (2)$$

in the formula (2), $Y^{21}$ represents a (meth)acryloyl group, a vinyl group or an allyl group; $Z^{21}$ represents an oxygen atom or a single bond; $R^{21}$ represents a single bond or an alkylene group having 1 to 12 carbon atoms which is linear, branched or has an aromatic ring;

$$—R^{22}—Z^{22}—Y^{22} \quad (3)$$

in the formula (3), $Y^{22}$ represents a (meth)acryloyl group, a vinyl group or an allyl group; $Z^{22}$ represents an oxygen atom or a single bond; $R^{22}$ represents a single bond or an alkylene group having 1 to 12 carbon atoms which is linear, branched or has an aromatic ring; wherein, $Y^{21}$ in the formula (2) and $Y^{22}$ in the formula (3) may be the same or different;

$$—X^{21}-E^{21}-X^{25}—R^{23}— \quad (4)$$

in the formula (4), $X^{31}$ and $X^{25}$ each independently represent a single bond, an oxygen atom or an alkylene glycol group; $E^{21}$ represents a —NHCO— group (in this case, $X^{21}$ represents a single bond; $X^{25}$ represents an oxygen atom or an alkylene glycol group; and $E^{21}$ forms an urethane bond together with $X^{25}$), a —CONH— group (in this case, $X^{21}$ represents an oxygen atom or an alkylene glycol group; $X^{25}$ represents a single bond; and $E^{21}$ forms an urethane bond together with $X^{21}$) or a bivalent group derived from diisocyanate selected from the set consisting of saturated or unsaturated aliphatic, alicyclic and aromatic groups (in this case, $X^{21}$ and $X^{25}$ each independently represent an oxygen atom or an alkylene glycol group; and $E^{21}$ forms an urethane bond between $X^{21}$ and $X^{25}$); and $R^{23}$ represents a linear or branched alkylene group having 1 to 6 carbon atoms;

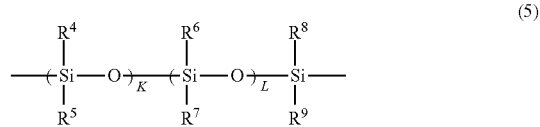
(5)

in the formula (5), $R^4$, $R^5$, $R^6$, $R^7$, $R^8$ and $R^9$ each independently represent an alkyl group having 1 to 6 carbon atoms, a fluorine-substituted alkyl group, a phenyl group or a hydrogen atom; K is of 10 to 100; L is 0 or of 1 to 90; and sum of K and L is of 10 to 100;

$$—R^{24}—X^{27}-E^{24}-X^{28}—R^{25}— \quad (6)$$

in the formula (6), $R^{24}$ and $R^{25}$ each independently represent a linear or branched alkylene group having 1 to 6 carbon atoms; $X^{27}$ and $X^{28}$ each independently represent oxygen atom or alkylene glycol group; $E^{24}$ represents a bivalent group derived from diisocyanate selected from the set consisting of saturated or unsaturated aliphatic, alicyclic and aromatic groups; in this case, $E^{24}$ forms two urethane bonds between $X^{27}$ and $X^{28}$;

$$—R^{26}—X^{26}-E^{22}-X^{22}— \quad (7)$$

in the formula (7), $R^{26}$ represents a linear or branched alkylene group having 1 to 6 carbon atoms; $X^{22}$ and $X^{26}$ each independently represent a single bond, an oxygen atom or an alkylene glycol group; $E^{22}$ represents a —NHCO— group (in this case, $X^{22}$ represents an oxygen atom or an alkylene glycol group; $X^{26}$ represents a single bond; and $E^{22}$ forms an urethane bond together with $X^{22}$), a —CONH— group (in this case, $X^{22}$ represents a single bond; $X^{26}$ represents an oxygen atom or an alkylene glycol group; and $E^{22}$ forms an urethane bond together with $X^{26}$) or a bivalent group derived from diisocyanate selected from saturated or unsaturated aliphatic, alicyclic and aromatic groups (in this case, $X^{22}$ and $X^{26}$ each independently represent an oxygen atom or an alkylene glycol group; and $E^{22}$ forms an urethane bond between $X^{22}$ and $X^{26}$.

In the above formula (1), $Y^{21}$ and $Y^{22}$ both represent a polymerizable group, and in light of capability of easy copolymerization with the hydrophilic compound having a polymerizable functional group of the component (B), an acryloyl group is particularly preferred.

In the above formula (1), $Z^{21}$ and $Z^{22}$ both represent an oxygen atom or a single bond, and is preferably an oxygen atom; $R^{21}$ and $R^{22}$ both represent a single bond or an alkylene group having 1 to 12 carbon atoms which is linear, branched or has an aromatic ring, and preferably an alkylene group having 2 to 4 carbon atoms; and $U^1$, $U^2$ and $U^3$ represent a group including an urethane bond in the molecular chain.

In $U^1$ and $U^3$ in the above formula (1), $E^{21}$ and $E^{22}$ each represent, as described above, a —CONH— group, a —NHCO— group or a bivalent group derived from diisocyanate selected from the set consisting of saturated or unsaturated aliphatic, alicyclic and aromatic groups. Examples of the bivalent group derived from diisocyanate selected from the set consisting of saturated or unsaturated aliphatic, alicyclic and aromatic groups include: bivalent groups derived from saturated aliphatic diisocyanate such as ethylene diisocyanate, 1,3-diisocyanatepropane, and hexamethylene diisocyanate; bivalent groups derived from alicyclic diisocyanate such as 1,2-diisocyanatecyclohexane, bis(4-isocyanatecyclohexyl)methane, and isophorone diisocyanate; bivalent groups derived from aromatic diisocyanate such as tolylene diisocyanate, and 1,5-diisocyanatenaphthalene; bivalent groups derived from unsaturated aliphatic diisocyanate such as 2,2'-diisocyanatediethyl fumarate. Of these examples, in light of being readily available and capable of imparting strength to the lens, bivalent groups derived from hexamethylene diisocyanate, bivalent groups derived from tolylene diisocyanate and bivalent groups derived from isophorone diisocyanate are preferred.

In $U^1$ in the above formula (1), when $E^{21}$ represent a —NHCO— group, $X^{21}$ represents a single bond; $X^{25}$ represents an oxygen atom or an alkylene glycol group; and $E^{21}$ forms an urethane bond represented by a formula: —NHCOO— together with $X^{25}$. Also, when $E^{21}$ represents a —CONH— group, $X^{21}$ represents an oxygen atom or an alkylene glycol group; $X^{25}$ represents a single bond; and $E^{21}$ forms an urethane bond represented by a formula: —OCONH— together with $X^{21}$. Further, when $E^{21}$ represents the aforementioned bivalent group derived from diisocyanate, $X^{21}$ and $X^{25}$ preferably, are each independently selected from an oxygen atom and an alkylene glycol group having 1 to 6 carbon atoms; $E^{21}$ forms an urethane bond between $X^{21}$ and $X^{25}$; and $R^{23}$ represents a linear or branched alkylene group having 1 to 6 carbon atoms.

In $U^2$ in the above formula (1), $E^{24}$ represents, as described above, a bivalent group derived from diisocyanate selected from the set consisting of saturated or unsaturated aliphatic, alicyclic and aromatic groups. Examples of the bivalent group derived from diisocyanate selected from the set consisting of saturated or unsaturated aliphatic, alicyclic and aromatic groups include similar bivalent groups to those exemplified in connection with $U^1$ and $U^3$ above. Of these examples, in light of being readily available and capable of imparting strength to the lens, bivalent groups derived from hexamethylene diisocyanate, bivalent groups derived from tolylene diisocyanate and bivalent groups derived from isophorone diisocyanate are preferred. In addition, $E^{24}$ forms two urethane bonds between $X^{27}$ and $X^{28}$. $X^{27}$ and $X^{28}$ preferably, each independently represent an oxygen atom or an alkylene glycol group having 1 to 6 carbon atoms, and $R^{24}$ and $R^{25}$ each independently represent a linear or branched alkylene group having 1 to 6 carbon atoms.

In $U^3$ in the above formula (1), $R^{26}$ represents a linear or branched alkylene group having 1 to 6 carbon atoms; when $E^{22}$ represents a —NHCO— group, $X^{22}$ represents an oxygen atom or an alkylene glycol group; $X^{26}$ represents a single bond; and $E^{22}$ forms an urethane bond represented by a formula: —NHCOO— together with $X^{22}$. Further, when $E^{22}$ represents a —CONH— group, $X^{22}$ represents a single bond; $X^{26}$ represents an oxygen atom or an alkylene glycol group; and $E^{22}$ forms an urethane bond represented by a formula: —OCONH— together with $X^{26}$. Moreover, when $E^{22}$ represents the aforementioned bivalent group derived from diisocyanate, $X^{22}$ and $X^{26}$ preferably, are each independently selected from an oxygen atom and an alkylene glycol group having 1 to 6 carbon atoms; and $E^{22}$ forms an urethane bond between $X^{22}$ and $X^{26}$.

The aforementioned $X^{21}$, $X^{25}$, $X^{27}$, $X^{28}$, $X^{22}$ and $X^{26}$ preferably represent alkylene glycol having 1 to 20 carbon atoms. Such alkylene glycol having 1 to 20 carbon atoms is represented by the following formula (8):

$$—O—(C_xH_{2x}—O)_y— \qquad (8)$$

(in the formula (8), x is of 1 to 4; and y is of 1 to 5.)

Examples of the groups in which the aforementioned $R^4$, $R^5$, $R^6$, $R^7$, $R^8$ and $R^9$ represent a fluorine-substituted alkyl group include groups represented by $—(CH_2)_m—C_pF_{2p+1}$  (wherein, m is of 1 to 10, and p is of 1 to 10). Specific examples of such a fluorine-substituted alkyl group include fluorine-substituted linear alkyl groups such as a 3,3,3-trifluoro-n-propyl group, a 2-(perfluorobutyl)ethyl group and a 2-(perfluorooctyl)ethyl group, fluorine-substituted branched alkyl groups such as a 2-(perfluoro-5-methylhexyl)ethyl group, and the like. When the compounding amount of the compound having a fluorine-substituted alkyl group is increased, the lipid-deposit resistance of the resulting lens can be improved.

In the above formula (5) representing $S^1$ and $S^2$, K is of 10 to 100; L is 0 or of 1 to 90; sum of K and L is of 10 to 100, and preferably 10 to 80. When sum of K and L is greater than 100, the molecular weight of the silicone compound becomes too large, solubility of the same with the hydrophilic compound as the component (B) may be impaired and phase separation can occur in polymerization to bring opaque, and thus failure in obtaining a uniform and transparent may be resulted. Whereas, when sum of K and L is less than 10, oxygen permeability of the resulting lens may be lowered, and the flexibility is also likely to deteriorate.

In the above formula (1), n is of 0 to 10, and preferably of 0 to 5. When n is greater than 10, the molecular weight of the silicone compound becomes too large, similarly to the aforementioned case, solubility of the same with the hydrophilic compound as the component (B) may be impaired and phase separation can occur in polymerization to bring opaque, and thus failure in obtaining a uniform and transparent may be resulted.

The silicone compound as the silicone compound (C) may have a hydrophilic partial structure in the molecule irrespective of the presence of the polymerizable functional group. Due to the silicone compound thus having a hydrophilic partial structure, solubility between the silicone compound and the hydrophilic polymer in the component (B) is improved, whereby wettability with water of the resulting lens can be improved. Examples of the hydrophilic partial structure of the silicone compound include polyethylene glycol, polypropylene glycol, polyvinyl alcohol, polyvinylpyrrolidone, poly(meth)acrylic acid, poly(meth)acrylic acid salt, poly(2-hydroxyethyl(meth)acrylate), polytetrahydrofuran, polyoxetane, polyoxazoline, polyacrylamide, polydimethylacrylamide, polydiethylacrylamide, poly(2-methacryloyloxyethylphosphorylcholine) and block polymers of the same, and the like. The hydrophilic partial structure may be alternately bound to the silicone compound, or may be bound at one end or both two ends. The molecular weight of the hydrophilic partial structure is preferably 100 to 1,000,000, and more preferably 1,000 to 500,000. When the molecular weight is less than 100, hydrophilicity sufficient for making compatible with the hydrophilic polymer in the component (B) may not be provided. On the other hand, when the molecular weight exceeds 1,000,000, each of the hydrophilic and hydrophobic domains becomes too great, and thus failure in obtaining a transparent material is likely to be resulted.

Examples of such a silicone compound include compounds represented by the following formula (9).

Typical examples of the silicone compound as the component (C) represented by the above formula (1) include compounds represented by the following formulae (C-1) and (C-2).

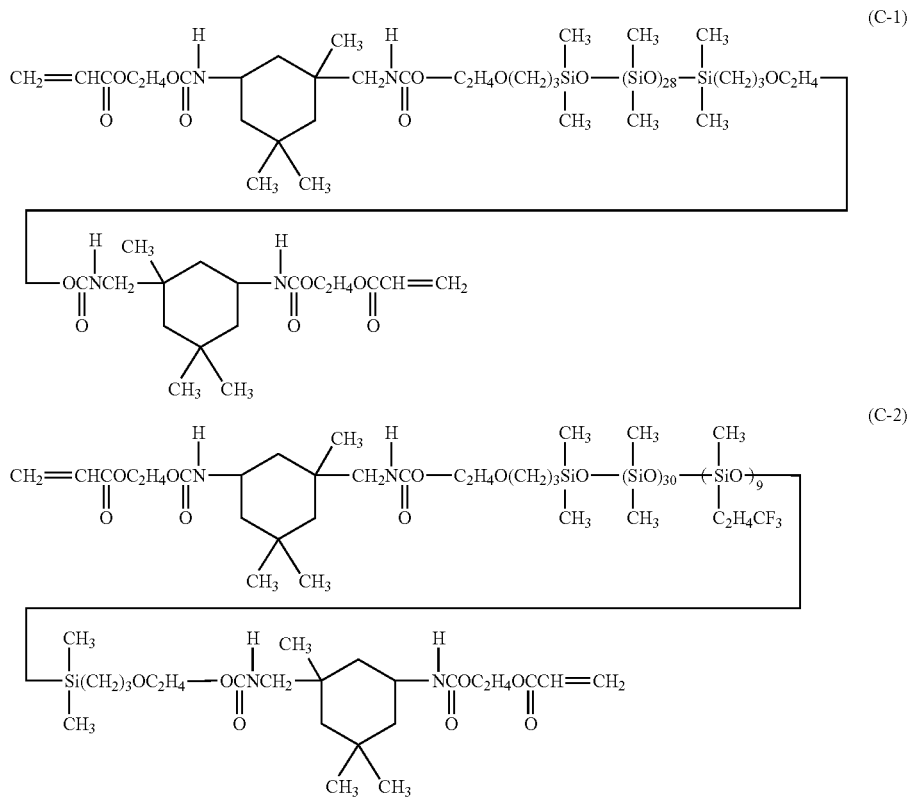

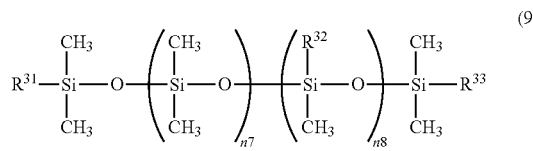

(in the formula (9), $R^{31}$, $R^{32}$ and $R^{33}$ each independently represent an alkyl group having 1 to 6 carbon atoms, hydrogen atom or a group represented by the following formula (10); n7 is of 5 to 100; n8 is of 0 to 100; and at least one of $R^{31}$, $R^{32}$ and $R^{33}$ is a group represented by the following formula (10).)

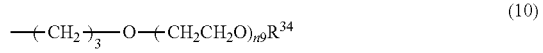

(in the formula (10), n9 is of 1 to 100; and $R^{34}$ represents an alkyl group having 1 to 22 carbon atoms or a hydrogen atom.)

In order to further improve the oxygen permeability of the resulting ophthalmic lens, and to impart flexibility thereto, other silicone compound may be contained in the composition in addition to the compound represented by the above formula (1). Examples of such other silicone compound include silicone-containing alkyl (meth)acrylate, silicone-containing styrene derivatives and silicone-containing fumaric acid diester.

Examples of the silicone-containing alkyl (meth)acrylate include trimethylsiloxydimethylsilylmethyl (meth) acrylate, trimethylsiloxydimethylsilylpropyl (meth)acrylate, methylbis(trimethylsiloxy)silylpropyl (meth) acrylate, tris(trimethylsiloxy)silylpropyl (meth) acrylate, mono[methylbis(trimethylsiloxy)siloxy]bis(trimethylsiloxy)silylpropyl (meth) acrylate, tris[methylbis(trimethylsiloxy)siloxy]silylpropyl (meth) acrylate, methylbis(trimethylsiloxy)silylpropylglyceryl (meth) acrylate, tris(trimethylsiloxy)silylpropylglyceryl (meth) acrylate, mono[methylbis(trimethylsiloxy)siloxy]bis(trimethylsiloxy)silylpropylglyceryl (meth) acrylate, trimethylsilylethyltetramethyldisiloxypropylglyceryl (meth) acrylate, trimethylsilylmethyl (meth)acrylate, trimethylsilylpropyl (meth) acrylate, trimethylsilylpropylglyceryl (meth) acrylate, trimethylsiloxydimethylsilylpropylglyceryl (meth) acrylate, methylbis(trimethylsiloxy)silylethyltetramethyldisiloxymethyl (meth) acrylate, tetramethyltriisopropylcyclotetrasiloxanyl propyl (meth) acrylate, tetramethyltriisopropylcyclotetrasiloxybis(trimethylsiloxy)silylpropyl (meth)acrylate, and the like.

Examples of the silicone-containing styrene derivative include compounds represented by the following formula (11), and the like.

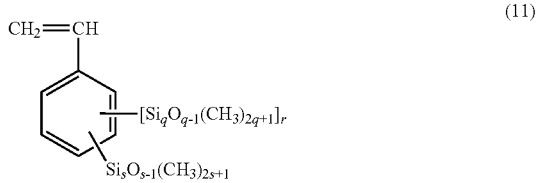

(11)

(in the formula (11), q is of 1 to 15; r is of 0 or 1; and s is of 1 to 15.)

Specific examples of the silicone-containing styrene derivative represented by the above formula (11) include tris(trimethylsiloxy)silylstyrene, bis(trimethylsiloxy)methylsilylstyrene, (trimethylsiloxy)dimethylsilylstyrene, tris(trimethylsiloxy)siloxydimethylsilylstyrene, [bis(trimethylsiloxy)methylsiloxy]dimethylsilylstyrene, (trimethylsiloxy)dimethylsilylstyrene, heptamethyltrisiloxanylstyrene, nonamethyltetrasiloxanylstyrene, pentadecamethylheptasiloxanylstyrene, heneicosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris(pentamethyldisiloxy)silylstyrene, tris(trimethylsiloxy)siloxybis(trimethylsiloxy)silylstyrene, bis(heptamethyltrisiloxy)methylsilylstyrene, tris[methylbis(trimethylsiloxy)siloxy]silylstyrene, trimethylsiloxybis[tris(trimethylsiloxy)siloxy]silylstyrene, heptakis(trimethylsiloxy)trisilylstyrene, nonamethyltetrasiloxyundecyl methylpentasiloxymethylsilylstyrene, tris[tris(trimethylsiloxy)siloxy]silylstyrene, (tristrimethylsiloxyhexamethyl)tetrasiloxy[tris(trimethylsiloxy)siloxy]trimethylsiloxysilylstyrene, nonakis(trimethylsiloxy)tetrasilylstyrene, bis(tridecamethylhexasiloxy)methylsilylstyrene, heptamethylcyclotetrasiloxanylstyrene, heptamethylcyclotetrasiloxybis(trimethylsiloxy)silylstyrene, tripropyltetramethylcyclotetrasiloxanylstyrene, trimethylsilylstyrene, and the like.

Examples of the silicone-containing fumaric acid diester include compounds represented by the following formula (12), and the like.

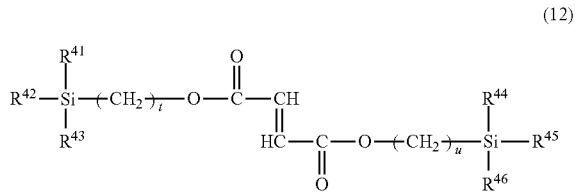

(12)

(in the formula (12), $R^{41}$, $R^{42}$, $R^{43}$, $R^{44}$, $R^{45}$ and $R^{46}$ each independently represent methyl group or a trimethylsiloxy group.)

Specific examples of the silicone-containing fumaric acid diester represented by the above formula (12) include bis(3-(trimethylsilyl)propyl)fumarate, bis(3-(pentamethylsisiloxanyl)propyl)fumarate, bis(tris(trimethylsiloxy)silylpropyl)fumarate, and the like.

The proportion of the silicone compound (C) used in the aforementioned composition is not particularly limited, but it is preferably no less than 5% by mass and no greater than 70% by mass, and more preferably no less than 10% by mass and no greater than 60% by mass. By including the silicone compound (C) at a proportion of no less than 5% by mass, a hydrogel having sufficient oxygen permeability and high flexibility can be obtained. When the proportion of the silicone compound (C) is no greater than 70% by mass, deterioration of the hydrophilicity, transparency and the like of the resulting lens can be prevented.

When further imparting another desired characteristic to the resulting ophthalmic lens is intended, alkyl (meth)acrylate, fluorine-containing alkyl (meth)acrylate, a hardness modifying monomer, a polymerizable ultraviolet ray-absorbing agent, a colorant, an ultraviolet ray-absorbing colorant and the like may be used as the monomer in a component (D).

Alkyl (meth)acrylate may be added to the composition in order to modify the hardness of the ophthalmic lens to impart a hard or soft property. Examples of the alkyl (meth)acrylate include linear, branched or cyclic alkyl (meth)acrylates such as methyl (meth)acrylate, ethyl (meth)acrylate, isopropyl (meth)acrylate, n-propyl (meth)acrylate, isobutyl (meth)acrylate, n-butyl (meth) acrylate, 2-ethylhexyl (meth) acrylate, n-octyl (meth) acrylate, n-decyl (meth)acrylate, n-dodecyl (meth)acrylate, t-butyl (meth)acrylate, pentyl (meth) acrylate, t-pentyl (meth)acrylate, hexyl (meth)acrylate, heptyl (meth)acrylate, nonyl (meth)acrylate, stearyl (meth) acrylate, cyclopentyl (meth)acrylate and cyclohexyl (meth) acrylate, and the like. These alkyl (meth)acrylates may be used either alone, or as a mixture of two or more thereof.

The fluorine-containing alkyl (meth)acrylate is added to the composition for the purpose of improving the lipid-deposit resistance of the ophthalmic lens. Examples of the fluorine-containing alkyl (meth)acrylate include compounds represented by the following formula (13), and the like.

(13)

(in the formula (13), $R^{51}$ represents a hydrogen atom or $CH_3$; v is of 1 to 15; and w is of 1 to (2v+1).)

Specific examples of the compound represented by the above formula (13) include 2,2,2-trifluoroethyl (meth)acrylate, 2,2,3,3-tetrafluoropropyl (meth) acrylate, 2,2,3,3-tetrafluoro-t-pentyl (meth)acrylate, 2,2,3,4,4,4-hexafluorobutyl (meth)acrylate, 2,2,3,4,4,4-hexafluoro-t-hexyl (meth)acrylate, 2,3,4,5,5,5-hexafluoro-2,4-bis(trifluoromethyl)pentyl (meth)acrylate, 2,2,3,3,4,4-hexafluorobutyl (meth) acrylate, 2,2,2,2',2',2'-hexafluoroisopropyl (meth)acrylate, 2,2,3,3,4,4-heptafluorobutyl (meth)acrylate, 2,2,3,3,4,4,5,5-octafluoropentyl (meth)acrylate, 2,2,3,3,4,4,5,5,5-nonafluoropentyl (meth)acrylate, 2,2,3,3,4,4,5,5,6,6,7,7-dodecafluoroheptyl (meth)acrylate, 3,3,4,4,5,5,6,6,7,7,8,8-dodecafluorooctyl (meth)acrylate, 3,3,4,4,5,5,6,6,7,7,8,8,8-tridecafluorooctyl (meth)acrylate, 2,2,3,3,4,4,5,5,6,6,7,7,7-tridecafluoroheptyl (meth)acrylate, 3,3,4,4,5,5,6,6,7,7,8,8,9,9,10,10-hexadecafluorodecyl (meth)acrylate, 3,3,4,4,5,5,6,6,7,7,8,8,9,9,10,10,10-heptadecafluorodecyl (meth) acrylate, 3,3,4,4,5,5,6,6,7,7,8,8,9,9,10,10,11,11-octadecafluoroundecyl (meth) acrylate, 3,3,4,4,5,5,6,6,7,7,8,8,9,9,10,10,11,11,11-nonadecafluoroundecyl (meth)acrylate, 3,3,4,4,5,5,6,6,7,7,8,8,9,9,10,10,11,11,12,12-eicosafluorododecyl (meth) acrylate, and the like. These fluorine-containing alkyl (meth) acrylates may be used either alone, or as a mixture of two or more thereof.

The proportion of the alkyl (meth)acrylate and the fluorine-containing alkyl (meth)acrylate used in the composition may be preferably no less than 0.01% by mass and no greater than 20% by mass, and more preferably no less than 0.1% by mass and no greater than 10% by mass. By adjusting the proportion of the alkyl (meth)acrylate or the fluorine-containing alkyl (meth)acrylate to be no less than 0.01% by mass, hardness of the ophthalmic lens can be appropriately modified, or the lipid-deposit resistance can be improved. On the other hand, by adjusting the proportion of the alkyl (meth) acrylate or the fluorine-containing alkyl (meth)acrylate to be no greater than 20% by mass, advantageous effects exerted by other components such as antibacterial property, transparency and oxygen permeability can be sufficiently achieved.

The hardness modifying monomer is added to the composition for the purpose of modifying the hardness of the ophthalmic lens to impart a hard or soft property. Examples of the hardness modifying monomer include: alkoxyalkyl (meth) acrylates such as 2-ethoxyethyl (meth) acrylate, 3-ethoxypropyl (meth)acrylate, 2-methoxyethyl (meth)acrylate and 3-methoxypropyl (meth)acrylate; alkylthioalkyl (meth)acrylates such as ethylthio ethyl (meth)acrylate and methylthioethyl (meth)acrylate; styrenes such as styrene, α-methylstyrene, methylstyrene, ethylstyrene, propylstyrene, butylstyrene, t-butylstyrene, isobutylstyrene, pentylstyrene, methyl-α-methylstyrene, ethyl-α-methylstyrene, propyl-α-methylstyrene, butyl-α-methylstyrene, t-butyl-α-methylstyrene, isobutyl-α-methylstyrene and pentyl-α-methylstyrene, and the like. These hardness modifying monomers may be used either alone, or as a mixture of two or more thereof.

The proportion of the hardness modifying monomer used in the composition may be preferably no less than 1% by mass and no greater than 30% by mass, and more preferably no less than 3% by mass and no greater than 20% by mass. By adjusting the proportion of the hardness modifying monomer to be no less than 1% by mass, a desired hard or soft property can be satisfactorily imparted to the ophthalmic lens. On the other hand, by adjusting the proportion of the hardness modifying monomer to be no greater than 30% by mass, deterioration of the oxygen permeability and mechanical strength of the ophthalmic lens can be inhibited.

The polymerizable ultraviolet ray-absorbing agent, the colorant and the ultraviolet ray-absorbing colorant may be added to the composition in order to impart the ultraviolet ray-absorptivity to the ophthalmic lens, or to tint the ophthalmic lens.

Examples of the polymerizable ultraviolet ray-absorbing agent include: benzophenone based polymerizable ultraviolet ray-absorbing agents such as 2-hydroxy-4-(meth)acryloyloxybenzophenone, 2-hydroxy-4-(meth)acryloyloxy-5-t-butylbenzophenone, 2-hydroxy-4-(meth)acryloyloxy-2',4'-dichlorobenzophenone and 2-hydroxy-4-(2'-hydroxy-3'-(meth)acryloyloxypropoxy)benzophenone; benzotriazole based polymerizable ultraviolet ray-absorbing agents such as 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole, 2-[3-(2H-benzotriazole-2-yl)-4-hydroxyphenyl]ethyl methacrylate, 2-(2'-hydroxy-5'-(meth) acryloyloxypropylphenyl)-2H-benzotriazole, 2-(2'-hydroxy-5'-(meth)acryloyloxypropyl-3'-t-butylphenyl)-5-chloro-2H-benzotriazole, 2-(2'-hydroxy-5'-(2"-methacryloyloxyethoxy)-3'-t-butylphenyl)-5-methyl-2H-benzotriazole and 2-[2'-hydroxy-5'-(2-methacryloyloxyethyl)phenyl]-2H-benzotriazole; salicylic acid derivative based polymerizable ultraviolet ray-absorbing agents such as phenyl 2-hydroxy-4-methacryloyloxymethylbenzoate; 2-cyano-3-phenyl-3-(3'-(meth)acryloyloxyphenyl)propenyl acid methyl ester, and the like. These polymerizable ultraviolet ray-absorbing agents may be used either alone, or as a mixture of two or more thereof.

Examples of the polymerizable colorant include azo polymerizable colorants such as 1-phenylazo-4-(meth)acryloyloxynaphthalene, 1-phenylazo-2-hydroxy-3-(meth)acryloyloxynaphthalene, 1-naphthylazo-2-hydroxy-3-(meth) acryloyloxynaphthalene, 1-(α-anthryl azo)-2-hydroxy-3-(meth)acryloyloxynaphthalene, 1-((4'-(phenylazo)-phenyl) azo)-2-hydroxy-3-(meth)acryloyloxynaphthalene, 1-(2',4'-xylylazo)-2-(meth)acryloyloxynaphthalene, 1-(o-tolylazo)-2-(meth)acryloyloxynaphthalene, 2-(m-(meth) acryloylamide-anilino)-4,6-bis(1'-(o-tolylazo)-2'-naphthylamino)-1,3,5-triazine, 2-(m-vinylanilino)-4-(4'-nitrophenylazo anilino)-6-chloro-1,3,5-triazine, 2-(1'-(o-tolylazo)-2'-naphthyloxy)-4-(m-vinylanilino)-6-chloro-1,3,5-triazine, 2-(p-vinylanilino)-4-(1'-(o-tolylazo)-2'naphthylamino)-6-chloro-1,3,5-triazine, N-(1'-(o-tolylazo)-2'-naphthyl)-3-vinylphthalic acidmonoamide, N-(1'-(o-tolylazo)-2'-naphthyl)-6-vinylphthalic acid monoamide, 3-vinylphthalic acid-(4'-(p-sulfophenylazo)-1'-naphthyl) monoester, 6-vinylphthalic acid-(4'-(p-sulfophenylazo)-1'-naphthyl) monoester, 3-(meth)acryloylamide-4-phenylazo phenol, 3-(meth)acryloylamide-4-(8'-hydroxy-3', 6'-disulfo-1'-naphthylazo)-phenol, 3-(meth)acryloylamide-4-(1'-phenylazo-2'-naphthylazo)-phenol, 3-(meth) acryloylamide-4-(p-tolylazo)phenol, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(m-(4'-hydroxy-1'-phenylazo)anilino)-6-isopropenyl-1,3, 5-triazine, 2-amino-4-(N-methyl-p-(4'-hydroxyphenylazo) anilino)-6-isopropenyl-1,3,5-triazine, 2-amino-4-(m-(3'-methyl-1'-phenyl-5'-hydroxy-4'-pyrazolylazo)anilino)-6-isopropenyl-1,3,5-triazine, 2-amino-4-(N-methyl-p-(3'-methyl-1'-phenyl-5'-hydroxy-4'-pyrazolyl azo)anilino)-6-isopropenyl-1,3,5-triazine, 2-amino-4-(p-phenylazo anilino)-6-isopropenyl-1,3,5-triazine and 4-phenylazo-7-(meth)acryloylamide-1-naphthol; anthraquinone polymerizable colorants such as 1,5-bis((meth)acryloylamino)-9,10-anthraquinone, 1-(4'-vinylbenzoylamide)-9,10-anthraquinone, 4-amino-1-(4'-vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(3'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis(4'-vinylbenzoylamide)-9,10-anthraquinone, 1,4-bis(4'-isopropenylbenzoylamide)-9,10-anthraquinone, 1,5'-bis(4'-vinylbenzoylamide)-9,10-anthraquinone, 1,5-bis(4'-isopropenylbenzoylamide)-9,10-anthraquinone, 1-methylamino-4-(3'-vinylbenzoylamide)-9, 10-anthraquinone, 1-methylamino-4-(4'-vinylbenzoyloxyethylamino)-9,10-anthraquinone, 1-amino-4-(3'-vinylphenylamino)-9,10-anthraquinone-2-sulfonic acid, 1-amino-4-(4'-vinylphenylamino)-9,10-anthraquinone-2-sulfonic acid, 1-amino-4-(2'-vinylbenzylamino)-9,10-anthraquinone-2-sulfonic acid, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 1-(3-ethoxycarbonylallylamino)-9,10-anthraquinone, 1-(β-carboxyallylamino)-9,10-anthraquinone, 1,5-di-(β-carboxyallylamino)-9,10-anthraquinone, 1-(3-isopropoxycarbonylallylamino)-5-benzoylamide-9,10-anthraquinone, 2-(3'-(meth) acryloylamide-anilino)-4-(3'-(3"-sulfo-4"-aminoanthraquinone-1"-yl)-amino-anilino)-6-chloro-1,3,5-triazine, 2-(3'-(meth)acryloylamide-anilino)-4-(3'-(3"-sulfo-4"-aminoanthraquinone-1"-yl)-amino-anilino)-6-hydrazino- 1,3,5-triazine, 2,4-bis-((4"-methoxyanthraquinon-1"-yl)-amino)-6-(3'-vinylanilino)-1,3,5-triazine and 2-(2'-vinylphenoxy)-4-(4'-(3"-sulfo-4"-aminoanthraquinon-1"-yl-amino)-anilino)-6-chloro-1,3,5-triazine; nitro polymerizable colorants such as o-nitroanilinomethyl (meth)acrylate; phthalocyanine polymerizable colorants such as (meth)acryloylated tetraaminocopper phthalocyanine and (meth)acryloylated (dodecanoylated tetraaminocopper phthalocyanine), and the like. These polymerizable colorants may be used either alone, or as a mixture of two or more thereof.

Examples of the polymerizable ultraviolet ray-absorbing colorant include benzophenone polymerizable ultraviolet ray-absorbing colorants such as 2,4-dihydroxy-3-(p-styrenoazo)benzophenone, 2,4-dihydroxy-5-(p-styrenoazo)benzophenone, 2,4-dihydroxy-3-(p-(meth)acryloyloxymethylphenylazo)benzophenone, 2,4-dihydroxy-5-(p-(meth)acryloyloxymethylphenylazo)benzophenone, 2,4-dihydroxy-3-(p-(meth)acryloyloxyethylphenylazo)benzophenone, 2,4-dihydroxy-5-(p-(meth)acryloyloxyethylphenylazo)benzophenone, 2,4-dihydroxy-3-(p-(meth)acryloyloxypropylphenylazo)benzophenone, 2,4-dihydroxy-5-(p-(meth)acryloyloxypropylphenylazo)benzophenone, 2,4-dihydroxy-3-(o-(meth)acryloyloxymethylphenylazo)benzophenone, 2,4-dihydroxy-5-(o-(meth)acryloyloxymethylphenylazo)benzophenone, 2,4-dihydroxy-3-(o-(meth)acryloyloxyethylphenylazo)benzophenone, 2,4-dihydroxy-5-(o-(meth)acryloyloxyethylphenylazo)benzophenone, 2,4-dihydroxy-3-(o-(meth)acryloyloxypropylphenylazo)benzophenone, 2,4-dihydroxy-5-(o-(meth)acryloyloxypropylphenylazo)benzophenone, 2,4-dihydroxy-3-(p-(N,N-di(meth)acryloyloxyethylamino)phenylazo)benzophenone, 2,4-dihydroxy-5-(p-(N,N-di(meth)acryloyloxyethylamino)phenylazo)benzophenone, 2,4-dihydroxy-3-(o-(N,N-di(meth)acryloyloxyethylamino)phenylazo)benzophenone, 2,4-dihydroxy-5-(o-(N,N-di(meth)acryloylethylamino)phenylazo)benzophenone, 2,4-dihydroxy-3-(p-(N-ethyl-N-(meth)acryloyloxyethylamino)phenylazo)benzophenone, 2,4-dihydroxy-5-(p-(N-ethyl-N-(meth)acryloyloxyethylamino)phenylazo)benzophenone, 2,4-dihydroxy-3-(o-(N-ethyl-N-(meth)acryloyloxyethylamino)phenylazo)benzophenone, 2,4-dihydroxy-5-(o-(N-ethyl-N-(meth)acryloyloxyethylamino)phenylazo)benzophenone, 2,4-dihydroxy-3-(p-(N-ethyl-N-(meth)acryloylamino)phenylazo)benzophenone, 2,4-dihydroxy-5-(p-(N-ethyl-N-(meth)acryloylamino)phenylazo)benzophenone, 2,4-dihydroxy-3-(o-(N-ethyl-N-(meth)acryloylamino)phenylazo)benzophenone, 2,4-dihydroxy-5-(o-(N-ethyl-N-(meth)acryloylamino)phenylazo)benzophenone, 2,4-dihydroxy-5-(4-(2-(N-(2-methacryloyloxyethyl)carbamoyloxy)ethyl)phenylazo)benzophenone and 2,4-dihydroxy-5-(4-(2-(N-(2-acryloyloxyethyl)carbamoyloxy)ethyl)phenylazo)benzophenone, benzoic acid polymerizable ultraviolet ray-absorbing colorants such as phenyl 2-hydroxy-4-(p-styrenoazo)benzoate, and the like. These polymerizable ultraviolet ray-absorbing colorants may be used either alone, or as a mixture of two or more thereof.

The proportion of the polymerizable ultraviolet ray-absorbing agent, the polymerizable colorant and the polymerizable ultraviolet ray-absorbing colorant used in the composition may be preferably no less than 0.01% by mass and no greater than 3% by mass, and more preferably no less than 0.01% by mass and no greater than 2% by mass. By adjusting the proportion of the polymerizable ultraviolet ray-absorbing agent, the polymerizable colorant and the polymerizable ultraviolet ray-absorbing colorant to be no less than 0.01% by mass, advantageous effects of the ultraviolet ray absorption and tinting can be satisfactorily achieved. On the other hand, by adjusting the proportion of these components to be no greater than 3% by mass, deterioration of the mechanical strength and transparency of the ophthalmic lens can be inhibited, and also the toxicity which may affect the living body can be prevented. It should be noted that when the lens has a low moisture content, and elution of the component is not found, a nonpolymerizable component such as 2-(4,6-diphenyl-1,3,5-triazine-2-yl)-5-(hexyloxy)phenol or 2-(5-chloro-2H-benzotriazole-2-yl)-6-(1,1-dimethylethyl)-4-methylphenol may be also used.

In order to regulate the crosslinking density, flexibility and the hard property of the resulting ophthalmic lens, a crosslinking agent may be added as a component (E). Examples of such a crosslinking agent include allyl methacrylate, vinyl methacrylate, 4-vinylbenzyl methacrylate, 3-vinylbenzyl methacrylate, methacryloyloxyethyl acrylate, ethylene glycol dimethacrylate, diethylene glycol dimethacrylate, diethylene glycol diallyl ether, triethylene glycol dimethacrylate, tetraethylene glycol dimethacrylate, propylene glycol dimethacrylate, dipropylene glycol dimethacrylate, butanediol dimethacrylate, trimethylolpropane trimethacrylate, 2,2-bis(p-methacryloyloxyphenyl)hexafluoropropane, 2,2-bis(m-methacryloyloxyphenyl)hexafluoropropane, 2,2-bis(o-methacryloyloxyphenyl)hexafluoropropane, 2,2-bis(p-methacryloyloxyphenyl)propane, 2,2-bis(m-methacryloyloxyphenyl)propane, 2,2-bis(o-methacryloyloxyphenyl)propane, 1,4-bis(2-methacryloyloxyhexafluoroisopropyl)benzene, 1,3-bis(2-methacryloyloxyhexafluoroisopropyl)benzene, 1,2-bis(2-methacryloyloxyhexafluoroisopropyl)benzene, 1,4-bis(2-methacryloyloxyisopropyl)benzene, 1,3-bis(2-methacryloyloxyisopropyl)benzene, 1,2-bis(2-methacryloyloxyisopropyl)benzene, and the like. These crosslinking agents may be used either alone, or as a mixture of two or more thereof.

The proportion of the crosslinking agent used in the composition may be preferably no less than 0.05% by mass and no greater than 1% by mass, and more preferably no less than 0.1% by mass and no greater than 0.8% by mass. By adjusting the proportion of the crosslinking agent to be no less than 0.05% by mass, adjustment of the flexibility and the like can be certainly carried out. On the other hand, by adjusting the proportion of the crosslinking agent to be no greater than 1% by mass, deterioration of the mechanical strength and durability of the ophthalmic lens can be inhibited.

The hydrogel that constitutes the ophthalmic lens may be obtained by heating and/or irradiating with ultraviolet rays to allow for copolymerization of a composition prepared by blending adequate amounts of the ionic compound (A), the hydrophilic compound as the component (B), the silicone compound as the silicone compound (C), the monomer in the component (D), and each polymerization component in the crosslinking agent as the component (E) in a cast molding process, and the swelling in water. Alternatively, it is also possible to carry out the copolymerization by irradiation with electron beams in place of the irradiation with ultraviolet rays.

When polymerizing each polymerization component by heating is to be carried out in the cast molding process, the aforementioned composition and a radical polymerization initiator are blended in a mold corresponding to a shape of a desired ophthalmic lens, and this mold is gradually heated to conduct polymerization. The molded product thus obtained may be subjected to mechanical processing such as cutting processing and grinding processing as needed, whereby an ophthalmic lens can be manufactured. The cutting may be carried out over the entire face of one or both two faces of the molded product (copolymer), or at a part of one or both two faces of the molded product. Exemplary polymerization process includes a bulk polymerization process and a solution polymerization process. However, since the ionic compound (A) which is generally in the form of an ionic liquid is used as a component for obtaining the copolymer, the bulk polymerization process carried out without using a solvent, or the solution polymerization process carried out hardly using a solvent may be adopted.

Examples of the solvent which may be used in the solution polymerization process include alcohols having 1 to 4 carbon atoms such as methanol, ethanol, 1-propanol and 2-propanol, and water soluble organic solvents such as acetone, methyl ethyl ketone, dimethyl formamide, dimethyl sulfoxide, acetonitrile and N-methyl-2-pyrrolidone. In light of acceleration of the copolymerization reaction and maintenance of homogeneity in the reaction liquid, these solvents may be used in an amount of preferably no less than 0.1 parts by mass and no greater than 50 parts by mass, and more preferably no less than 0.5 parts by mass and no greater than 15 parts by mass with respect to 100 parts by mass of the entire polymerization components of the composition.

Examples of the radical polymerization initiator which may be used in the polymerization by heating include 2,2'-azobisisobutyronitrile, 2,2'-azobis(2,4-dimethylvaleronitrile), benzoyl peroxide, t-butyl hydroperoxide, cumene hydroperoxide, lauroyl peroxide, t-butylperoxyhexanoate, 3,5,5-trimethylhexanoyl peroxide, and the like. These radical polymerization initiators may be used either alone, or as a mixture of two or more thereof. The amount of the radical polymerization initiator used may be adjusted to preferably no less than about 0.001 parts by mass and no greater than 2 parts by mass, and more preferably no less than 0.01 parts by mass and no greater than 1 part by mass with respect to 100 parts by mass of the entire polymerization components of the composition.

The heating temperature when the composition within the mold is heated may be preferably no lower than 50° C. and no higher than 150° C., and more preferably no lower than 60° C. and no higher than 140° C. Also, the heating time when the composition within the mold is heated may be preferably no less than 10 min and no greater than 120 min, and more preferably no less than 20 min and no greater than 60 min. By setting the heating temperature within the mold at no lower than 50° C., or heating time for no less than 10 min, polymerization time can be shortened, and decrease of residual monomer components can be contemplated. On the other hand, by setting the heating temperature within the mold at no higher than 150° C., or heating time for no greater than 120 min, volatilization of each polymerization component can be suppressed, and deformation of the mold can be prevented.

When polymerizing each polymerization component by irradiating with ultraviolet rays is to be carried out in the cast molding process, the aforementioned composition and a photopolymerization initiator are blended in a mold corresponding to a shape of a desired ophthalmic lens, and thereafter this mold is irradiated with ultraviolet rays to conduct polymerization. The molded product thus obtained may be subjected to mechanical processing such as cutting processing and grinding processing as needed, whereby an ophthalmic lens can be manufactured. Similarly to the polymerization by heating, the cutting may be carried out over the entire face of one or both two faces of the molded product, and any process of a bulk polymerization process and a solution polymerization process may be employed also in such polymerization by irradiating with ultraviolet rays.

The material entity of the mold which may be used in the polymerization by irradiation with ultraviolet rays is not particularly limit as long as it is a material entity that can transmit ultraviolet rays necessary for polymerization and curing, and is preferably a multi-purpose resin such as polypropylene, polystyrene, nylon or polyester and may be glass. Such a material is molded, followed by processing to give a mold having a desired shape.

After the composition containing each polymerization component, a photopolymerization initiator, and a solvent as needed are blended in such a mold, ultraviolet rays are irradiated to carry out the polymerization. The wavelength range of the ultraviolet rays can be selected in accordance with the function of the ophthalmic lens material. However, it is necessary to select the type of the employed photopolymerization initiator depending on the wavelength range of the ultraviolet rays irradiated. The illuminance of the ultraviolet rays may be preferably no less than $1.0$ mW/cm$^2$ and no greater than 50 mW/cm$^2$. The ultraviolet rays having different illuminances may be irradiated stepwise. Also, the irradiation time of the ultraviolet rays is at least 1 minute. Such illuminance of the ultraviolet rays and irradiation time enable the composition to be sufficiently cured while the material is prevented from deterioration. Moreover, the composition may be heated concurrently with the irradiation with the ultraviolet rays, whereby the polymerize reaction is accelerated, and thus the copolymer can be readily formed.

Examples of the photopolymerization initiator for use in polymerization by irradiating with ultraviolet rays include: phosphine oxide type photopolymerization initiators such as 2,4,6-trimethylbenzoyl-diphenylphosphine oxide (TPO) and bis(2,4,6-trimethylbenzoyl)-phenylphosphine oxide; benzoin type photopolymerization initiators such as methyl orthobenzoyl benzoate, methylbenzoyl formate, benzoin methyl ether, benzoin ethyl ether, benzoin isopropyl ether, benzoin isobutyl ether and benzoin n-butyl ether; phenone type photopolymerization initiators such as 2-hydroxy-2-methyl-1-phenylpropan-1-one, p-isopropyl-α-hydroxyisobutylphenone, p-t-butyltrichloroacetophenone, 2,2-dimethoxy-2-phenylacetophenone and α,α-dichloro-4-phenoxyacetophenone, N,N-tetraethyl-4,4-diaminobenzophenone; 1-hydroxycyclohexyl phenyl ketone; 1-phenyl-1,2-propanedion-2-(o-ethoxycarbonyl)oxime; thioxanthone type photopolymerization initiators such as 2-chlorothioxanthone and 2-methylthioxanthone; dibenzosuberone; 2-ethylanthraquinone; benzophenone acrylate; benzophenone; benzyl, and the like. These photopolymerization initiators may be used either alone, or as a mixture of two or more thereof. In addition, a photosensitizer may be also used together with the photopolymerization initiator. The proportion of these photopolymerization initiator and photosensitizer may be preferably no less than about 0.001 parts by mass and no greater than 2 parts by mass, and more preferably no less than 0.01 parts by mass and no greater than 1 part by mass with respect to 100 parts by mass of the entire polymerization components of the composition.

In order to improve the surface characteristics of the ophthalmic lens, a low-temperature plasma treatment, atmospheric pressure plasma, corona discharge and the like may be carried out. By subjecting to a low-temperature plasma treatment, an ophthalmic lens that is more superior in wettability with water and/or stain resistance can be obtained. The low-temperature plasma treatment may be carried out in an atmosphere of dilute gas such as alkane and alkane substituted with fluorine each having 1 to 6 carbon atoms, nitrogen, oxygen, argon, hydrogen, air, water, silane or a mixture thereof. In particular, it is preferred that a low-temperature plasma treatment is carried out in an atmosphere of dilute gas such as oxygen alone, or a mixture of oxygen with water, tetrafluoromethane, organic silane, methane, nitrogen or the like, for a reason that the effects of physical surface modification by ion etching, and of chemical surface modification by radical implantation are expected. The low-temperature plasma treatment may be carried out either under reduced pressure, or under atmospheric pressure. According to the low-temperature plasma treatment, the effects of surface modification can be controlled by appropriately adjusting output power, treatment time and gas concentration at high frequency wave RF (for example, 13.56 MHz), low frequency wave AF (for example, 15.0 to 40.0 KHz), and micro wave (for example, 2.45 GHz).

In preparing an ophthalmic lens material, a bulk polymerization process or a solution polymerization process may be used. In the bulk polymerization process, the viscosity of the system extremely increases in accordance with proceeding of the polymerization, and thus a large amount of monomers remain which failed to be diffused in the highly viscous system and thus cannot be participated in the polymerization reaction. Whereas, according to the solution polymerization process, since the solvent is not participated in the reaction, the solvent inevitably remains in the lens. In manufacture of contact lenses which are a medical device, for the purpose of reducing the amount of these residues as low as possible, a treatment of immersing a contact lens in water or an organic solvent or a mixed solution of these, preferably repeating this process to allow the residues to be eluted is carried out to remove the residues from the contact lens. As a solvent for use in such a treatment, an aqueous solution dissolving an inorganic compound such as physiological saline solution, or a mixed solution of the same with an organic solvent may be also used.

The linear swelling coefficient in water of the ophthalmic lens obtained in this manner becomes smaller than the linear swelling coefficient in water of the ophthalmic lens in which the fluorine-containing anion is replaced for an anion not containing fluorine. Although not bound any theory, this low linear expansion rate is believed to result from inhibition of steric enlargement of molecules in the hydrogel due to low polarity of the fluorine-containing anion. By thus restricting the linear swelling coefficient in water of the ophthalmic lens at a low level, more comfortable wearing feel of the lens can be attained, and also deterioration of wearing feel due to ease in drying that results from the ophthalmic lens having a high linear swelling coefficient, as well as development of eye diseases such as defects caused by dry eye can be prevented beforehand.

According to the ophthalmic lens, the difference between the linear swelling coefficient in water of the ophthalmic lens in which the fluorine-containing anion was replaced for an anion not containing fluorine and the linear swelling coefficient in water of the ophthalmic lens before the replacement is preferably no less than 0.005 and no greater than 0.1. By thus adjusting the difference between the linear swelling coefficient in water of the ophthalmic lens in which the fluorine-containing anion was replaced for an anion not containing fluorine and the linear swelling coefficient in water of the ophthalmic lens before the replacement to be no less than 0.005, the moisture content of the lens can be maintained to fall within an appropriate range, and maintaining the flexibility as a hydrogel at a high level is enabled. In contrast, adjusting the difference between the linear swelling coefficient in water of the ophthalmic lens in which the fluorine-containing anion was replaced for an anion not containing fluorine, and the linear swelling coefficient in water of the ophthalmic lens before the replacement to be no greater than 0.1 enables further improvement of the wearing feel, and prevention of the eye disease.

As described in the foregoing, the ophthalmic lens exhibits superior antibacterial properties owing to the cation and the fluorine-containing anion included as components of the hydrogel. Also, since the ophthalmic lens is integrally formed from a hydrogel in the entirety of the lens, it can be easily manufactured with extra costs being saved. Still further, due to the fluorine-containing anion included in the hydrogel, the ophthalmic lens has a significantly low linear swelling coefficient in water, and thus comfortable wearing feel can be achieved. Therefore, the ophthalmic lens of the present invention can be suitably used for a contact lens, as well as an artificial cornea, cornea onlay, cornea inlay, and the like.

EXAMPLES

Hereinafter, the present invention is more specifically explained by way of Examples, but the present invention is not limited to the following Examples.
[Components Used]
Meanings of abbreviations used in the following Examples are shown below.
  HEMA: 2-hydroxyethyl methacrylate
  EDMA: ethylene glycol dimethacrylate
  HMPPO: 2-hydroxy-2-methyl-1-phenylpropane-1-one
  Macromonomer A (urethane-containing siloxane macromer): compound represented by the above formula (C-1)
  TRIS: tris(trimethylsiloxy)silylpropyl methacrylate
  DMAA: N,N-dimethyl acrylamide
  N-MMP: N-methyl-3-methylene-2-pyrrolidinone (1-methyl-3-methylene-2-pyrrolidone)
  BVI-TFSI (3-butyl-1-vinylimidazoliumbis(trifluoromethanesulfonyl)imide): compound represented by the above formula (II), wherein $R^2$ represents $-CH=CH_2$, n3 is 4, $R^B$ represents a hydrogen atom, and $X^2$ represents TFSI (anion represented by the above formula (V))
  BVI-Br (3-butyl-1-vinylimidazolium bromide): compound represented by the above formula (II), wherein $R^2$ represents $-CH=CH_2$, n3 is 4, $R^B$ represents a hydrogen atom, and $X^2$ represents Br
  BVI-Cl (3-butyl-1-vinylimidazolium chloride): compound represented by the above formula (II), wherein $R^2$ represents $-CH=CH_2$, n3 is 4, $R^B$ represents a hydrogen atom, and $X^2$ represents Cl
  OVI-TFSI (3-octyl-1-vinylimidazolium bis(trifluoromethanesulfonyl)imide): compound represented by the above formula (II), wherein $R^2$ represents $-CH=CH_2$, n3 is 8, $R^B$ represents a hydrogen atom, and $X^2$ represents TFSI (anion represented by the above formula (V))
  OVI-Br (3-octyl-1-vinylimidazolium bromide): compound represented by the above formula (II), wherein $R^2$ represents $-CH=CH_2$, n3 is 8, $R^B$ represents a hydrogen atom, and $X^2$ represents Br
  HDVI-TFSI (3-hexadecyl-1-vinylimidazolium bis(trifluoromethanesulfonyl)imide): compound represented by the above formula (II), wherein $R^2$ represents $-CH=CH_2$, n3 is 16, $R^B$ represents a hydrogen atom, and $X^2$ represents TFSI (anion represented by the above formula (V))
  MDOA-TFSI (2-methacryloyloxyethyldimethyloctylammonium bis(trifluoromethanesulfonyl)imide): compound represented by the above formula (I), wherein $R^1$ represents $-CH_3$, n1 is 2, n2 is 8, $R^A$ represents a hydrogen atom, Y represents $-O-$, and $X^1$ represents TFSI (anion represented by the above formula (V))

MDOA-Br (2-methacryloyloxyethyldimethyloctylammonium bromide): compound represented by the above formula (I), wherein $R^1$ represents —$CH_3$, n1 is 2, n2 is 8, $R^4$ represents a hydrogen atom, Y represents —O—, and $X^1$ represents Br ADCA-TFSI (2-acryloyloxyethyldimethylcetylammonium bis(trifluoromethanesulfonyl)imide): compound represented by the above formula (I), wherein $R^1$ represents —H, n1 is 2, n2 is 16, $R^4$ represents a hydrogen atom, Y represents —O—, and $X^1$ represents TFSI (anion represented by the above formula (V))

ADCA-Br (2-acryloyloxyethyldimethylcetylammonium bromide): compound represented by the above formula (I), wherein $R^1$ represents —H, n1 is 2, n2 is 16, $R^4$ represents a hydrogen atom, Y represents —O—, and $X^1$ represents Br MOI-TFSI (1-(2-methacryloyloxyethyl)-3-octylimidazolium bis(trifluoromethanesulfonyl)imide): compound represented by the above formula (II), wherein $R^2$ represents a group represented by the formula (IV), which is a 2-methacryloyloxyethyl group ($H_2C$=$C(CH_3)$—C (=O)—O—$CH_2$—$CH_2$—) wherein $R^3$ represents —$CH_3$, and n5 is 2; n3 is 8, $R^B$ represents a hydrogen atom; and $X^2$ represents TFSI (anion represented by the above formula (V))

VOP-Br (4-vinyl-1-octylpyridinium bromide): compound represented by the above formula (III), wherein n4 is 7, $X^3$ represents Br VOP-TFSI (4-vinyl-1-octylpyridinium bis(trifluoromethanesulfonyl)imide): compound represented by the above formula (III), wherein n4 is 8, $R^c$ represents a hydrogen atom, and $X^3$ represents TFSI (anion represented by the above formula (V))

ADHA-TFSI 2-acryloyloxyethyldimethyl(11-hydroxyundecyl)ammonium bis(trifluoromethanesulfonyl)imide: compound represented by the above formula (I), wherein $R^1$ represents —H, n1 is 2, n2 is 10, $R^4$ represents —OH, Y represents —O—, and $X^1$ represents TFSI (anion represented by the above formula (V))

ADUA-TFSI 2-acryloyloxyethyldimethyl (11-carboxyundecyl)ammonium bis(trifluoromethanesulfonyl)imide: compound represented by the above formula (I), wherein $R^1$ represents —H, n1 is 2, n2 is 10, $R^4$ represents —COOH, Y represents —O—, and $X^1$ represents TFSI (anion represented by the above formula (V))

Example 1

A blend liquid was prepared by homogeneously mixing 90 parts by mass of HEMA, 0.3 parts by mass of EDMA, 0.3 parts by mass of HMPPO, and 10 parts by mass of BVI-TFSI to permit dissolution. This blend liquid was injected into a mold for contact lens made from a polypropylene resin, and polymerization was allowed using an ultraviolet ray irradiation apparatus (UV Curing System UBX0302-03 manufactured by Eye Graphics Co., Ltd.) equipped with an ultraviolet ray lamp having a dominant wavelength at 365 nm with a illuminance of about 10 mW/cm² for about 20 min. After the lens was released from the mold, it was immersed in distilled water in a volume of 2 mL per lens. About 16 hours later, the lens was transferred into a physiological saline solution having a concentration of 0.9% by mass. About additional 6 hours later, the lens was transferred into a physiological saline solution having the same concentration prepared separately, and subjected to autoclave sterilization. Accordingly, a transparent soft contact lens (hydrogel) was obtained.

Example 2

HEMA in an amount of 100 parts by mass of, 0.4 parts by mass of EDMA, 0.3 parts by mass of HMPPO, and 1.0 part by mass of sodium methacrylate were homogeneously mixed to permit dissolution. With 90 parts by mass of this solution were homogeneously mixed 10 parts by mass of MDOA-TFSI to permit dissolution, whereby a blend liquid was prepared. A soft contact lens was obtained in a similar manner to Example 1 using this blend liquid.

Example 3

A polymerizable composition A was prepared by homogeneously mixing 33 parts by mass of macromonomer A (urethane-containing siloxane macromer), 22 parts by mass of TRIS, 10 parts by mass of DMAA, 35 parts by mass of N-MMP, 0.4 parts by mass of EDMA and 0.4 parts by mass of HMPPO to permit dissolution. For preparing a blend liquid, 85 parts by mass of the polymerizable composition A, 5 parts by mass of BVI-TFSI, and 10 parts by mass of isopropanol were mixed and dissolved to give a blend liquid. This blend liquid was injected into a mold for contact lens made from a polypropylene resin, and polymerization was allowed using a ultraviolet ray irradiation apparatus (UV Curing System UBX0302-03 manufactured by Eye Graphics Co., Ltd.) equipped with an ultraviolet ray lamp having a dominant wavelength at 365 nm with a illuminance of about 10 mW/cm² for about 20 min. After the lens was released from the mold, the lens was subjected to a plasma treatment (manufactured by Kyoto Denshi Keisoku K. K., low temperature ashing apparatus PA-102AT; conditions: 0.8 Torr $O_2$, output: 50 W, treatment time: 2 min), and then immersed in distilled water in a volume of 2 mL per lens. About 16 hours later, the lens was transferred into a physiological saline solution having a concentration of 0.9% by mass. About additional 6 hours later, the lens was transferred into a physiological saline solution having the same concentration prepared separately, and subjected to autoclave sterilization. Accordingly, a transparent soft contact lens (hydrogel) was obtained.

Example 4

A soft contact lens was obtained in a similar manner to Example 3 using as the blend liquid a solution prepared by mixing 85 parts by mass of the polymerizable composition A, 5 parts by mass of OVI-TFSI, and 10 parts by mass of isopropanol to permit dissolution.

Example 5

A soft contact lens was obtained in a similar manner to Example 3 using as the blend liquid a solution prepared by mixing 75 parts by mass of the polymerizable composition A, 10 parts by mass of MOI-TFSI, and 15 parts by mass of isopropanol to permit dissolution.

Example 6

A soft contact lens was obtained in a similar manner to Example 3 using as the blend liquid a solution prepared by mixing 100 parts by mass of the polymerizable composition A and 0.1 parts by mass of HDVI-TFSI to permit dissolution.

Example 7

A soft contact lens was obtained in a similar manner to Example 3 using as the blend liquid a solution prepared by mixing 99 parts by mass of the polymerizable composition A, and 1 part by mass of HDVI-TFSI to permit dissolution.

Example 8

A soft contact lens was obtained in a similar manner to Example 3 using as the blend liquid a solution prepared by mixing 95 parts by mass of the polymerizable composition A, and 5 parts by mass of MDOA-TFSI to permit dissolution.

Example 9

A soft contact lens was obtained in a similar manner to Example 3 using as the blend liquid a solution prepared by mixing 100 parts by mass of the polymerizable composition A and 0.1 parts by mass of ADCA-TFSI to permit dissolution.

Example 10

A soft contact lens was obtained in a similar manner to Example 3 using as the blend liquid a solution prepared by mixing 99 parts by mass of the polymerizable composition A, and 1 part by mass of ADCA-TFSI to permit dissolution.

Example 11

A soft contact lens was obtained in a similar manner to Example 3 using as the blend liquid a solution prepared by mixing 95 parts by mass of the polymerizable composition A, and 5 parts by mass of ADCA-TFSI to permit dissolution.

Example 12

A soft contact lens was obtained in a similar manner to Example 3 using as the blend liquid a solution prepared by mixing 80 parts by mass of the polymerizable composition A, and 20 parts by mass of ADCA-TFSI to permit dissolution.

Example 13

A soft contact lens was obtained in a similar manner to Example 3 using as the blend liquid a solution prepared by mixing 95 parts by mass of the polymerizable composition A, and 5 parts by mass of VOP-TFSI to permit dissolution.

Example 14

A soft contact lens was obtained in a similar manner to Example 3 using as the blend liquid a solution prepared by mixing 95 parts by mass of the polymerizable composition A, and 5 parts by mass of ADHA-TFSI to permit dissolution.

Example 15

A soft contact lens was obtained in a similar manner to Example 3 using as the blend liquid a solution prepared by mixing 95 parts by mass of the polymerizable composition A, and 5 parts by mass of ADUA-TFSI to permit dissolution.

Comparative Example 1

A soft contact lens was obtained in a similar manner to Example 1 using as the blend liquid a solution prepared by mixing 100 parts by mass of HEMA, 0.3 parts by mass of EDMA, and 0.3 parts by mass of HMPPO to permit dissolution.

Comparative Example 2

A soft contact lens was obtained in a similar manner to Example 3 using as the blend liquid a solution prepared by mixing 90 parts by mass of the polymerizable composition A, and 10 parts by mass of isopropanol to permit dissolution.

Comparative Example 3

A soft contact lens was obtained in a similar manner to Example 3 using as the blend liquid the polymerizable composition A alone.

Comparative Example 4

Although as the blend liquid 85 parts by mass of the polymerizable composition A, BVI-Br5 parts by mass, 10 parts by mass of isopropanol were mixed, a not homogeneously dissolved but opaque solution was prepared, and thus production of a transparent lens failed.

Comparative Example 5

Although as the blend liquid 85 parts by mass of the polymerizable composition A, 5 parts by mass of BVI-Cl, and 10 parts by mass of isopropanol were mixed, a not homogeneously dissolved but opaque solution was prepared, and thus production of a transparent lens failed.

Comparative Example 6

Although as the blend liquid 85 parts by mass of the polymerizable composition A, 5 parts by mass of OVI-Br, and 10 parts by mass of isopropanol were mixed, a not homogeneously dissolved but opaque solution was prepared, and thus production of a transparent lens failed.

Comparative Example 7

Although as the blend liquid 95 parts by mass of the polymerizable composition A, and 5 parts by mass of ADCA-Br were mixed, a not homogeneously dissolved but opaque solution was prepared, and thus production of a transparent lens failed.

Comparative Example 8

Although as the blend liquid 85 parts by mass of the polymerizable composition A, 5 parts by mass of MDOA-Br, and 10 parts by mass of isopropanol were mixed, a not homogeneously dissolved but opaque solution was prepared, and thus production of a transparent lens failed.

Comparative Example 9

Although as the blend liquid 85 parts by mass of the polymerizable composition A, 5 parts by mass of VOP-Br, and 10 parts by mass of isopropanol were mixed, a not homogeneously dissolved but opaque solution was prepared, and thus production of a transparent lens failed.

[Evaluation of Antibacterial Property]
<Preparation of SCDA Medium>

To 400 mL of purified water was added 16.0 g of Soybean-Casein Digest Agar Medium (manufactured by Nihon Pharmaceutical Co., Ltd.), and the mixture was subjected to steam sterilization under pressure at 121° C. for 20 min.

<Preparation of 500-fold Diluted Nutrient Broth (1/500 NB medium)>

To 100 mL of purified water was added 1.8 g of nutrient broth (manufactured by Eiken Chemical Co., Ltd.), and the solution was heated to permit dissolution. Thereafter, an aliquot of 1 mL of the solution was drawn and diluted to 500-fold, and the diluted solution was subjected to steam sterilization under pressure at 121° C. for 20 min.

<Preparation of Bacterial Suspension for Inoculation>

1) A colony was picked up from a master plate of a bacterial strain (Staphylococcus aureus NBRC13276), and smeared on an SCDA medium.

2) The SCDA medium on which the colony was smeared was precultured at 35±2° C.

3) The bacterial cells precultured on the SCDA medium were suspended in a 1/500 NB medium, and adjusted to give the viable cell counts of about $10^8$ cfu/mL on the basis of transmittance at 660 nm. Furthermore, the bacterial cell liquid was diluted using the 1/500 NB medium such that the viable cell counts became $1.0 \times 10^4$ to $1.4 \times 10^4$ cfu/mL to prepare a bacterial liquid for inoculation.

<Antibacterial Property Test of Lens>

The lenses produced in Examples 1 to 15 and Comparative Examples 1 to 3 were subjected to the following operation.

1) A predetermined pieces of the lens and the bacterial liquid for inoculation were placed into a vial so as to satisfy the relationship represented by the following formula:

(surface area of the lens)/(bacterial liquid for inoculation)=32 cm$^2$/10 mL.

2) The cap of the vial was closed, and subjected to shaking culture at 35±2° C. and at 150 rpm for about 24 hours.

3) After completing the culture, 1 mL of the bacterial liquid was collected, and serially diluted with the 1/500 NB medium, followed by inoculation on an SCDA medium and culturing at 35±2° C.

4) The number of colonies thus detected was counted to determine viable cell counts.

The results on each of the lenses are shown in Table 1 below.

TABLE 1

|  | viable cell counts (cells) |
| --- | --- |
| Example 1 | $2.3 \times 10^3$ |
| Example 2 | $1.8 \times 10^2$ |
| Comparative Example 1 | $3.7 \times 10^4$ |
| Example 3 | $9.4 \times 10^3$ |
| Example 4 | $7.6 \times 10^3$ |
| Example 5 | $5.7 \times 10^3$ |
| Comparative Example 2 | $8.8 \times 10^4$ |
| Example 6 | $3.4 \times 10^3$ |
| Example 7 | 6 |
| Example 8 | $1.4 \times 10^4$ |
| Example 9 | $1.2 \times 10^4$ |
| Example 10 | 6 |
| Example 11 | 2 |
| Example 12 | 0 |
| Example 13 | $1.3 \times 10^4$ |
| Example 14 | $1.2 \times 10^2$ |
| Example 15 | $3.6 \times 10^2$ |
| Comparative Example 3 | $1.5 \times 10^5$ |

As is clear from Table 1, viable cell counts evidently decreased in: Examples 1 and 2 as compared with Comparative Example 1; Example 3, 4 and 5 as compared with Comparative Example 2; and Examples 6 to 15 as compared with Comparative Example 3, revealing that proliferation of the bacteria was effectively suppressed.

Example 16

A blend liquid was prepared by homogeneously mixing 30 parts by mass of glycerol methacrylate, 70 parts by mass of HEMA, 0.5 parts by mass of EDMA and 0.4 parts by mass of HMPPO, and 5 parts by mass of BVI-TFSI to permit dissolution. This blend liquid was injected into a mold for contact lens made from a polypropylene resin, and polymerization was allowed using a ultraviolet ray irradiation apparatus (UV Curing System UBX0302-03 manufactured by Eye Graphics Co., Ltd.) equipped with an ultraviolet ray lamp having a dominant wavelength at 365 nm with a illuminance of about 10 mW/cm$^2$ for about 20 min. After the lens was released from the mold, it was immersed in distilled water at 20° C., and lest to stand until reaching equilibrium swelling to obtain a soft contact lens (hydrogel).

Example 17

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of OVI-TFSI to permit dissolution.

Example 18

A soft contact lens reaching equilibrium swelling was obtained in a similar manner to Example 16 using as the blend liquid a solution prepared by mixing a solution prepared by mixing 30 parts by mass of glycerol methacrylate, 70 parts by mass of HEMA, 0.5 parts by mass of EDMA and 0.4 parts by mass of HMPPO, and 5 parts by mass of MDOA-TFSI to permit dissolution.

Example 19

A soft contact lens reaching equilibrium swelling was obtained in a similar manner to Example 16 using as the blend liquid a solution prepared by mixing a solution prepared by mixing 30 parts by mass of glycerol methacrylate, 70 parts by mass of HEMA, 0.5 parts by mass of EDMA and 0.4 parts by mass of HMPPO, and 5 parts by mass of ADCA-TFSI to permit dissolution.

Comparative Example 10

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of BVI-Cl to permit dissolution.

Comparative Example 11

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of BVI-Br to permit dissolution.

Comparative Example 12

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of OVI-Br to permit dissolution.

Comparative Example 13

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of MDOA-Br to permit dissolution.

Comparative Example 14

A soft contact lens reaching equilibrium swelling was obtained in a similar manner to Example 16 using as the blend liquid a solution prepared by mixing 30 parts by mass of glycerol methacrylate, 70 parts by mass of HEMA, 0.5 parts by mass of EDMA and 0.4 parts by mass of HMPPO, and 5 parts by mass of ADCA-Br to permit dissolution.

[Evaluation of Linear Swelling Coefficient]

After the copolymerization in Examples 16 to 19 and Comparative Examples 10 to 14, and the mold release subsequent thereto, the rate of the lens diameter when reaching equilibrium swelling at 20° C., with respect to the lens diameter in a dry state prior to immersion in distilled water was calculated, and the rate was determined as the linear swelling coefficient represented by the following formula:

Linear swelling coefficient=(Lens diameter after hydration)/(Lens diameter before hydration).

The results are shown in Table 2 below.

TABLE 2

|  | Linear Expansion Rate |
| --- | --- |
| Example 16 | 1.283 |
| Comparative Example 10 | 1.368 |
| Comparative Example 11 | 1.328 |
| Example 17 | 1.276 |
| Comparative Example 12 | 1.284 |
| Example 18 | 1.274 |
| Comparative Example 13 | 1.311 |
| Example 19 | 1.274 |
| Comparative Example 14 | 1.298 |

As is clear from Table 2, it was revealed that the expansion rate in water was significantly reduced in: Example 16 as compared with Comparative Examples 10 and 11; Example 17 as compared with Comparative Example 12; Example 18 as compared with Comparative Example 13; and Example 19 as compared with Comparative Example 14.

INDUSTRIAL APPLICABILITY

The ophthalmic lens of the present invention has antibacterial properties and transparency, as well as a small linear swelling coefficient in water; therefore, it is suitably used for a contact lens. In addition, use in wide variety of applications such as artificial corneas, cornea onlay and cornea inlay is possible.

The invention claimed is:

1. An ophthalmic lens integrally formed with a hydrogel, the hydrogel including a copolymer obtained from a composition comprising
   (A) an ionic compound including a cation having a polymerizable functional group and a fluorine-containing anion, and
   (B) a hydrophilic compound having a polymerizable functional group,
   the copolymer being obtained through copolymerization of the ionic compound (A) and the hydrophilic compound (B).

2. The ophthalmic lens according to claim 1, wherein the cation having a polymerizable functional group is at least one selected from the set consisting of an imidazolium ion, a pyridinium ion and a quaternary ammonium ion.

3. The ophthalmic lens according to claim 1, wherein the ionic compound (A) is a compound represented by the following formulae (I):

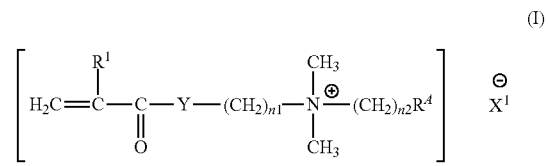

wherein in the formula (I), R' represents —H or —CH$_3$; Y represents —O— or —NH—; n1 is of 1 to 18; n2 is of 1 to 25; X' represents an anion including fluorine; and R$^4$ represents a hydrogen atom, —OH or —COOH.

4. The ophthalmic lens according to claim 1, wherein the fluorine atom-containing anion is an anion represented by the following formula (V),

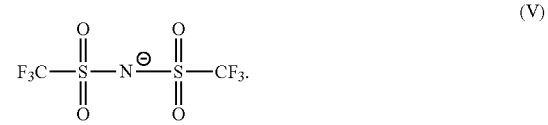 [SMILES: O=S(=O)([N-]S(=O)(=O)C(F)(F)F)C(F)(F)F]

5. The ophthalmic lens according to claim 1, wherein the composition further comprises
   (C) a silicone compound.

6. The ophthalmic lens according to claim 1, wherein the ionic compound (A) is an ionic liquid.

7. The ophthalmic lens according to claim 1, wherein the linear swelling coefficient in water is less than the linear swelling coefficient in water of the ophthalmic lens in which the fluorine-containing anion was replaced for an anion not containing fluorine.

8. The ophthalmic lens according to claim 1, wherein the difference between the linear swelling coefficient in water of the ophthalmic lens in which the fluorine-containing anion was replaced for an anion not containing fluorine, and the linear swelling coefficient in water of the ophthalmic lens before the replacement is no less than 0.005 and no greater than 0.1.

9. The ophthalmic lens according to claim 1, the ophthalmic lens being for use as a contact lens.

* * * * *